(12) United States Patent
Salehpoor

(10) Patent No.: US 12,121,655 B2
(45) Date of Patent: Oct. 22, 2024

(54) ACTIVE LUNG ASSIST DEVICE

(71) Applicant: Karim Salehpoor, Bakersfield, CA (US)

(72) Inventor: Karim Salehpoor, Bakersfield, CA (US)

( * ) Notice: Subject to any disclaimer, the term of this patent is extended or adjusted under 35 U.S.C. 154(b) by 843 days.

(21) Appl. No.: 17/241,433

(22) Filed: Apr. 27, 2021

(65) Prior Publication Data

US 2022/0031983 A1 Feb. 3, 2022

Related U.S. Application Data

(60) Provisional application No. 63/018,397, filed on Apr. 30, 2020.

(51) Int. Cl.
*A61M 16/00* (2006.01)
*A61M 16/10* (2006.01)
*A61M 16/20* (2006.01)

(52) U.S. Cl.
CPC .... *A61M 16/0063* (2014.02); *A61M 16/1005* (2014.02); *A61M 16/1065* (2014.02); *A61M 16/208* (2013.01); *A61M 16/209* (2014.02); *A61M 2016/0027* (2013.01)

(58) Field of Classification Search
CPC .......... A61M 16/0063; A61M 16/1005; A61M 16/0072; A61M 16/0075; A61M 16/208; A61M 16/209; A61M 16/009; A61M 16/0084; A61M 16/0081
See application file for complete search history.

(56) References Cited

U.S. PATENT DOCUMENTS

| | | | |
|---|---|---|---|
| 4,340,044 A * | 7/1982 | Levy | A61M 16/024 128/205.15 |
| 4,459,982 A | 7/1984 | Fry | |
| 6,135,967 A | 10/2000 | Fiorenza et al. | |
| 7,934,499 B2 | 5/2011 | Berthon-Jones | |
| 10,549,100 B2 | 2/2020 | Dimarco | |
| 10,729,865 B2 | 8/2020 | Bahns et al. | |
| 10,946,159 B2 | 3/2021 | Christopher et al. | |

* cited by examiner

*Primary Examiner* — Kendra D Carter
*Assistant Examiner* — Maap Ahmed Ellabib
(74) *Attorney, Agent, or Firm* — Andrew D. Fortney; Central California IP Group, P.C.

(57) ABSTRACT

An active breathing assistance apparatus is disclosed. A simple apparatus includes first, second and third sets of balloons in a base compartment; a compression component on or over the balloons, configured to expel air from the balloons; a tubing network connected to the balloons; a wearable breathing compartment at an outlet of the tubing network; first and second check valves in the tubing network, between the breathing compartment and (i) the third set of balloons and (ii) the first and/or second balloons, respectively; third and fourth check valves between atmospheric air and the first and second balloons, respectively; a cover securing the compression component to the base compartment; and a motion restricting component controlling movement of the compression component. The first and second sets of balloons are between the compression component and the base compartment, and the third set of balloons is between the compression component and the cover.

7 Claims, 6 Drawing Sheets

ACTIVE LUNG ASSIST DEVICE

CROSS REFERENCE TO RELATED APPLICATIONS

This Application claims Priority of patent application Ser. No. 63/018,397 filed on Apr. 30, 2020.

BACKGROUND OF THE INVENTION

1. Field of the Invention

The present invention relates to an Active lung Assist Device for actively (i.e., forcefully) supplying breathable air or oxygen into the lungs of a user patient who experiences acute or chronic respiratory problems, and/or actively (i.e., forcefully) removing or sucking out carbon dioxide and other gaseous and non-gaseous contents of the air sacs (alveoli) of the lungs, and therefore assist the biological lungs of the user patient in maintaining their gas exchange functionality even if the said biological lungs cannot expand or contract as usual on their own. The Active Lung Assist Device can be used to support individual user patients; it can also be used to support multiple user patients (mass user patients) simultaneously. The Active Lung Assist Device can be operated manually, or by using powered components and devices.

2. Description of the Prior Art

Respiratory devices have been used to support the supply of air or oxygen to patients in hospitals or at homes when the said patients are not been able to maintain their normal breathing on their own. Such respiratory devices supply air or oxygen to a patient's biological lung to support the inhalation step of the breathing, however, they rely on the said biological lung itself for the exhalation step of the breathing.

U.S. Pat. No. 6,135,967 describes a respiratory ventilator with automatic flow calibration and methodology for monitoring breath flow and automatically regulating and calibrating respiration gas flow delivery. The ventilator includes a gas flow calibration member, a reader component for recording inspiratory and exhalation gas volume, and a gas flow calibration member.

The respiratory ventilator with automatic flow calibration, described above, is a device that can calibrate a flowing respiratory gas and in doing so it relies on the function of the biological lung to set the said respiratory gas in flow; the device is not meant for removing carbon dioxide and other gaseous substances from the biological lung if the said lung is unable to expand or contract on its own to expel its gaseous contents. Additionally, the device is not meant for removing any non-gaseous substances that might accumulate in the said biological lung gradually.

U.S. Pat. No. 4,459,982 describes a servo-controlled demand regulator for respiratory ventilator and a mechanism for a respiratory ventilator by which the gas delivery mechanism can cause delivery of gas to the patient either at a predetermined flow rate or at a rate that is directly controlled by the patient's instantaneous demand.

The servo-controlled demand regulator for respiratory ventilator, described above, is a device that cause delivery of a gas at a desired rate; it is not meant for removing carbon dioxide and other gaseous substances from a biological lung if the said lung is unable to function on its own to expel its gaseous contents. Additionally, the device is not meant for removing any non-gaseous substances that might accumulate in the said biological lung gradually.

U.S. Pat. No. 10,946,159 B2 describes a system for providing flow-targeted ventilation synchronized to a patient's breathing cycle for providing ventilation in a predetermined flow waveform synchronized to a patient's breathing cycle to augment respiration by a self-breathing patient.

The system for providing flow-targeted ventilation synchronized to a patient's breathing cycle, described above, is an invasive device that can provide ventilation for a self-breathing patient; it is not meant for providing ventilation to patients with impaired biological lungs that are not able to breath on their own.

U.S. Pat. No. 10,729,865 B2 describes a device for the pressure-supported or pressure-controlled ventilation of a patient with reduced spontaneous breathing. The device receives signals from an EMG unit as a function of the patient's breathing effort which are used to deliver a breathing gas with a preset pressure.

The device for the pressure-supported or pressure-controlled ventilation of a patient with reduced spontaneous breathing, described above, relies on a patient's breathing effort; it is not meant for providing ventilation to patients with impaired biological lungs that are not able to breath on their own.

U.S. Pat. No. 10,549,100 B2 describes a system and method for activating inspiratory and expiratory muscle function to restore breathing and coughing by using electrical stimulation system to electrically stimulate inspiratory and expiratory muscle motor neurons in a subject. The device includes both internally and externally mounted components.

The system and method for activating inspiratory and expiratory muscle function, described above, is an invasive system that can stimulate inspiratory and expiratory muscles. For electrical muscle stimulation to successfully induce inspiration and expiration, the muscles must be capable of responding to electrical stimulus at a frequency sufficient for breathing and for as long as such stimulated breathing is necessary.

U.S. Pat. No. 7,934,499 B2 describes a patient-ventilator synchronization using dual phase sensors that employs standard fuzzy logic method and measures respiratory airflow and the respiratory effort to deliver ventilatory support that is synchronized with the phase of the patient's respiratory efforts for targeting a minimum ventilation.

The patient-ventilator synchronization using dual phase sensors, described above, relies on existence of a respiratory airflow to modify the said airflow; it is not meant for providing ventilation to patients with impaired biological lungs that are not able to establish any respiratory airflow on their own.

Examination of the prior art reviles methods and devices that have been proposed for supporting respiratory needs of individual patients. These devices and methods often provide inspiratory support with the expiration effort done by the patient's biological lungs. There are instances in which a biological lung is unable to contribute to the expiratory step of the breathing. Examples are when construction crew become partially buried in soil in a collapsed trench in which the soil pressure prevents chest movements, thus breathing becomes impossible. Unfortunately, these cases result in death if the construction crew cannot be pulled out of soil quickly and gently. Another example is when liquid accumulates within air sacs (alveoli) of the lung, thus it impairs the gas exchange in the lung. There are also pandemic situations, such as COVID-19, in which there is not enough individual ventilators to care for many patients at a time. Therefore, there is a need for an Active Lung Assist Device that can provide active expiration and inspiration to support respiratory needs for patients who have impaired lung functionality and cannot establish any necessary respiratory airflow on their own, or to people whose chest movements are prevented, or to people whose lungs cannot perform necessary respiratory gas exchange because of liquid accumulation in air sacs (alveoli) of their lungs. Additionally, there is also a need for an Active Lung Assist Device, that is built as a central unit, to provide active expiration and inspiration to support respiratory needs for many patients, simultaneously, in emergency and permanent healthcare facilities or during respiratory pandemic situations.

SUMMARY OF THE INVENTION

The present invention is an Active Lung Assist Device that can be used to support inspiration and expiration, actively, for individual or group of patients and people who cannot or have difficulty to breath on their own.

The Active Lung Assist Device can prevent accumulation of any liquid or non-gaseous substances within the air sacs (alveoli) of the lungs of the user patient and can thus maintain the lungs' gas exchange capability even if the lungs' air sacs (alveoli) have lost their elasticity and the lungs are not capable of maintaining acts of inhalation and/or exhalation on their own.

The Active Lung Assist Device can support inspiration and expiration in people or patients even if the chest movements of the said people or patients are restricted.

Building at the right scale, the Active Lung Assist Device can serve hundreds or thousands of patients simultaneously, thus it will be a solution to a global pandemic situation such as the Coronavirus pandemic.

The Active Lung Assist Device may include and use combination of its automated mechanical, electrical, and computerize control and monitoring systems for safe functioning of the device; additionally, the trained attending health care crew can fix functional problems of the Device, on their own, as much as they can if the automated monitoring components have not been included in the Active Lung Assist Device.

The Device can provide a quick relief in pandemic respiratory diseases as well as in respiratory disorders in which lungs cannot function on their own, because of accumulation of excessive fluid in lungs' air sacs (alveoli), by suctioning the accumulated fluid in the lungs in a short time, thus enable the lungs to resume their gas exchange functionality on their own in a short time.

All embodiments or alternatives of embodiments of the Active Lung Assist Device supply positive pressure or vacuum pressure, to a user patient, that do not cause any damage to the alveoli of the lungs of the said user patient or make the said alveoli collapse to the extent that prevents the said lungs from functioning.

Any component or combination of components of any embodiments or alternatives of any embodiment of the Active Lung Assist Device can be disinfected in situ by circulating a disinfecting substance through the said components or combination of components, or those components or combination of components can be separated from the rest of the components of the Active Lung Assist Device for disinfecting elsewhere, as desired.

All embodiments or alternatives of embodiments of the Active Lung Assist Device can be built as a stationary or mobile device.

All necessary equipment and instrumentation will be used to assure that all embodiments or alternatives of embodiments of the Active Lung Assist Device function safely and expectedly, as desired.

It is therefore a primary object of the present invention to provide an Active Lung Assist Device that can be used to support respiratory needs of individual patients who are not capable of or have difficulty to breath on their own.

It is another object of the present invention to provide an Active Lung Assist Device that can be used to support respiratory needs of multiple patients, simultaneously, who are not capable of or have difficulty to breath on their own.

It is a further object of the present invention to provide an Active Lung Assist Device that is equipped with a fluid pressurizing component, a pressurized compartment containing pressurized breathable gas, a vacuum pump, and a vacuum compartment to supply breathable gas to the lungs of user patients or suction out undesired substances from the lungs of the said patients to support their expiration and inspiration actively.

It is still another object of the present invention to provide an Active Lung Assist Device that is equipped with directional valves, a pressurized compartment, a vacuum compartment, and a wearable breathing compartment to provide active inspiration and expiration for user patients.

It is still a further object of the present invention to provide an Active Lung Assist Device that can be used to support inspiration and expiration for patients or people that cannot breath on their own because their chest movements have become restricted.

It is yet another object of the present invention to provide an Active Lung Assist Device that can be used to support inspiration and expiration of patients or people whose lungs' air sacs (alveoli) are flooded with liquid thus have impaired gas exchange capability.

It is yet a further object of the present invention to provide an Active Lung Assist Device that can be used to support inspiration and expiration of patients who have impaired lung functionality because the tissue and air sacs (alveoli) of their lungs have lost their elastic properties and therefore cannot contract or expand on their own to support inspiration and expiration of the said patients on their own.

DETAILED DESCRIPTION OF THE INVENTION

1. Definitions

Breathable gas as used herein shall mean a body of air, or oxygen, or any mixture of desired gases that is conditioned to safe pressure, temperature, and humidity and can be inhaled by patients to support their respiratory needs without having any negative impact on the function of any biological organ of the said patients.

Breathable air as used herein shall mean a body of air that is at a safe pressure, temperature, and humidity and can be inhaled by patients to support their respiratory needs without having any negative impact on the function of any biological organ of the said patients.

Air as used herein shall mean a body of air that is at a safe pressure, temperature, and humidity and can be inhaled by patients to support their respiratory needs without having any negative impact on the function of any biological organ of the said patients.

Oxygen as used herein shall mean the gaseous oxygen element, or its mixture with any other gaseous substance, that is at a safe pressure, temperature, and humidity and can be inhaled by patients to support their respiratory needs without having any negative impact on the function of any biological organ of the said patients.

User patient as used herein shall mean any person or patient that uses any embodiment of the Active Lung Assist Device to support their respiratory needs.

Mass user(s) as used herein shall mean multiple user patients that use the Active Lung Assist Device, simultaneously, to support their respiratory needs.

Fluid moving device as used herein shall mean any type of device, equipped with any type of powering unit, that can move fluids from one location to another location thus increase or decrease pressure at the said location. Examples of fluid moving devices are compressors and vacuum pumps, each with their powering units.

Vacuum as used herein shall mean any pressure that is less than the atmospheric pressure by magnitude.

2. Best Mode of the Invention

Figure 1A:
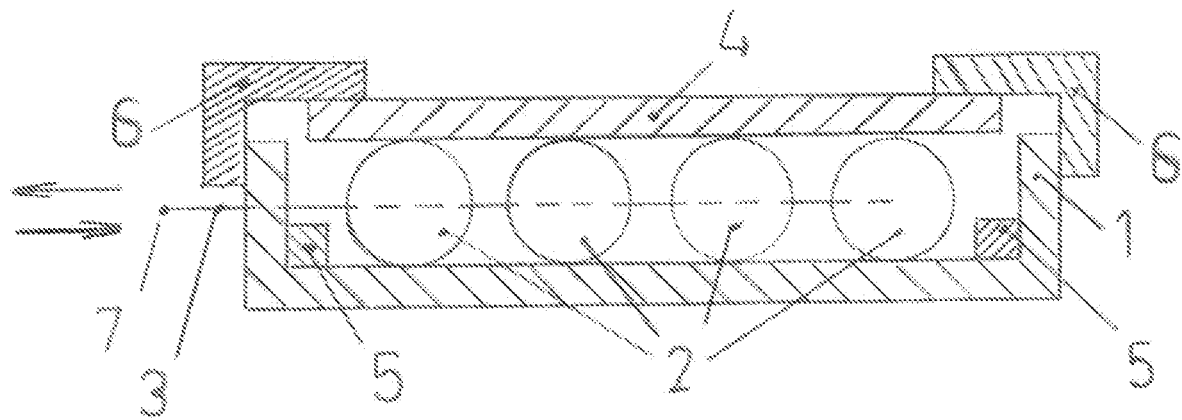
FIG. 1A and FIG. 1B show simplified schematics of the Manual Exhalation embodiment of the Active Lung Assist Device.
Figure 1B:
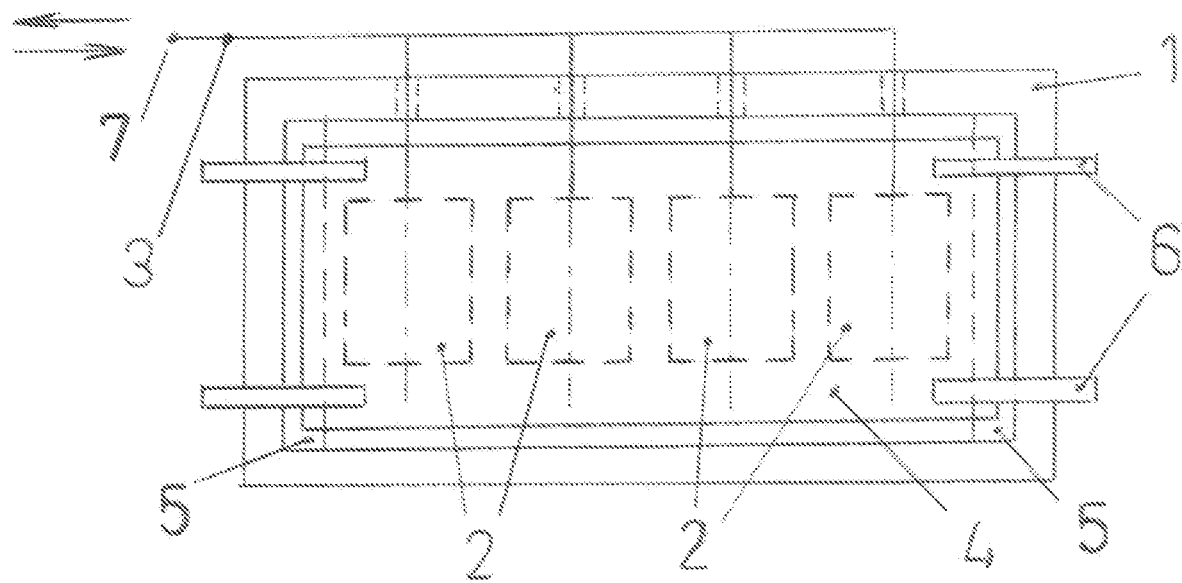

FIG. 1A and FIG. 1B show the best mode of the Manual Exhalation embodiment of the Active Lung Assist Device.

Figure 2:
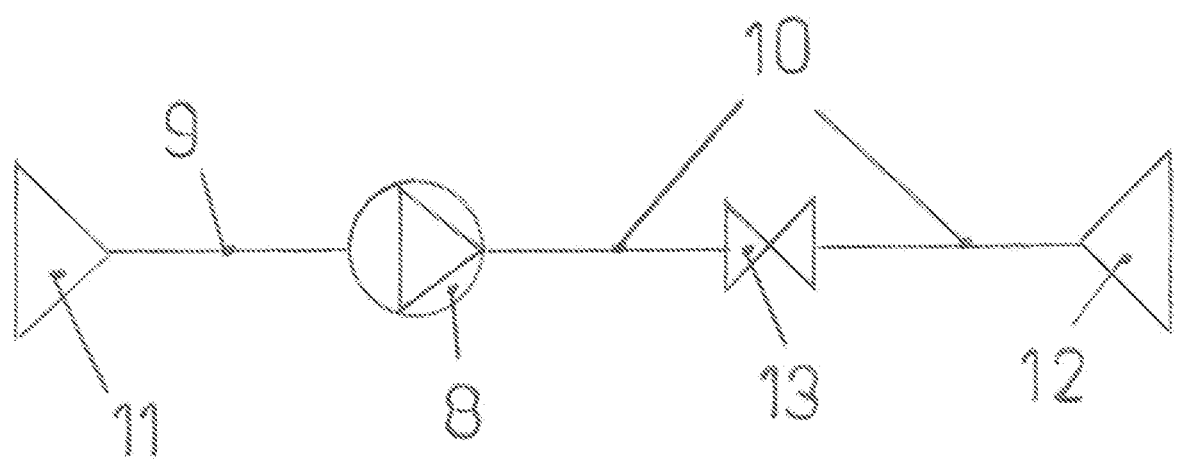
FIG. 2 shows simplified schematic of the Powered, Non-Automatic, Inhalation-Exhalation embodiment of the Active Lung Assist Device.

FIG. 2 shows the best mode of the Powered, Non-Automatic, Inhalation-Exhalation embodiment of the Active Lung Assist Device.

Figure 3A:
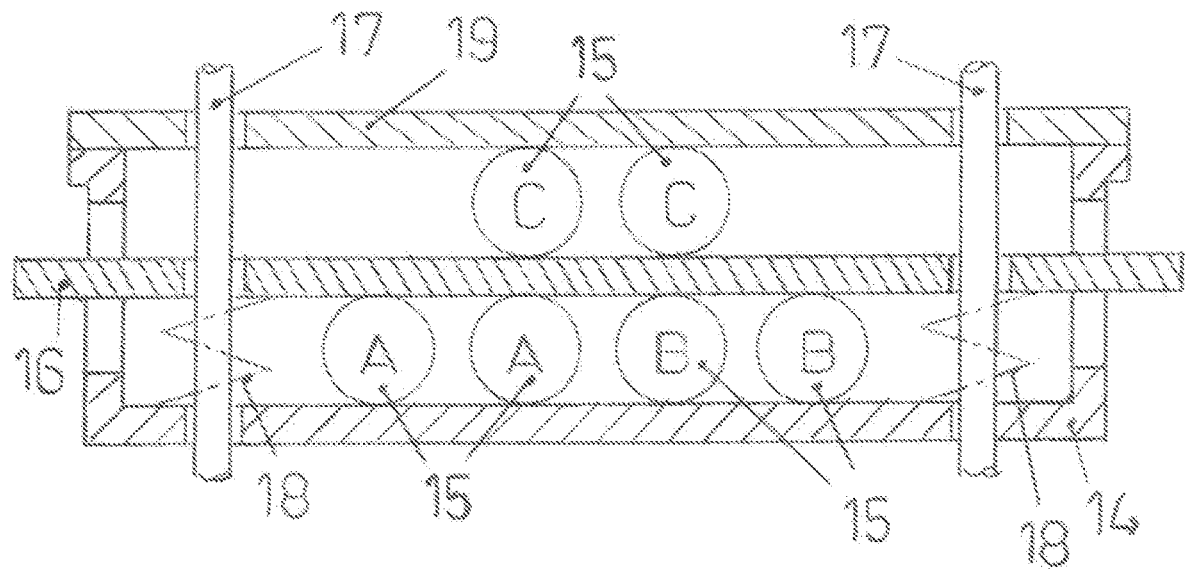
FIG. 3A, FIG. 3B, and FIG. 3C show simplified schematics of the Manual Inhalation-Exhalation embodiment of the Active Lung Assist Device.
Figure 3B:
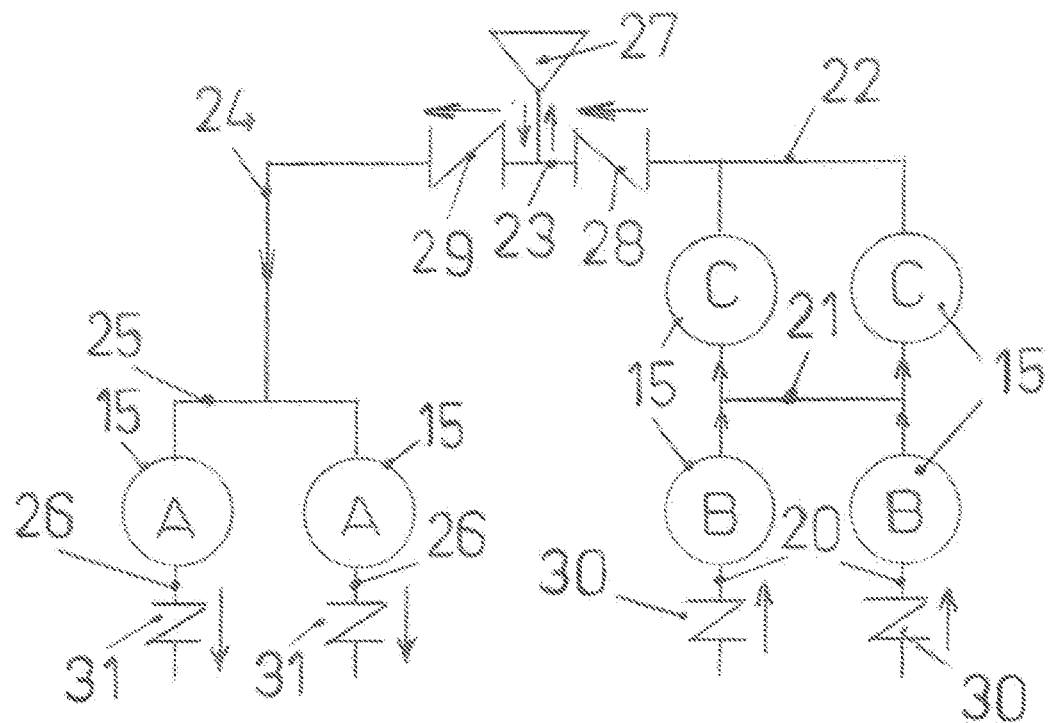
Figure 3C:
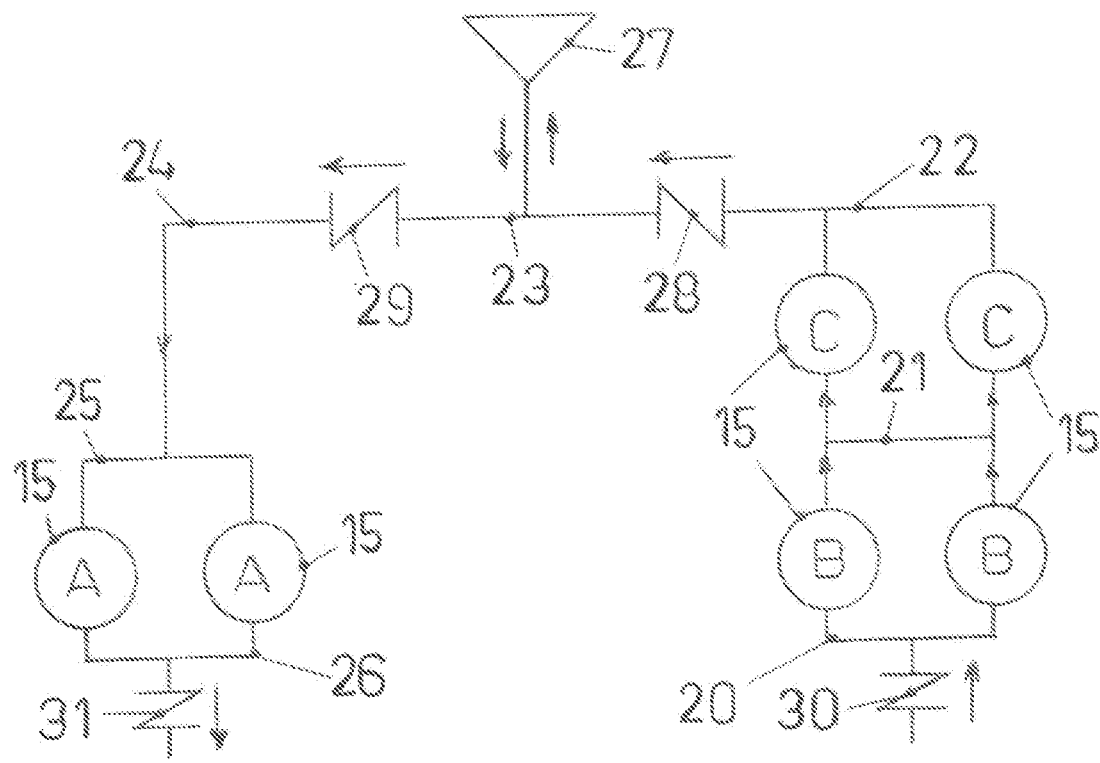

FIG. 3A, FIG. 3B, and FIG. 3C show the best mode of the Manual Inhalation-Exhalation embodiment of the Active Lung Assist Device.

Figure 3D:
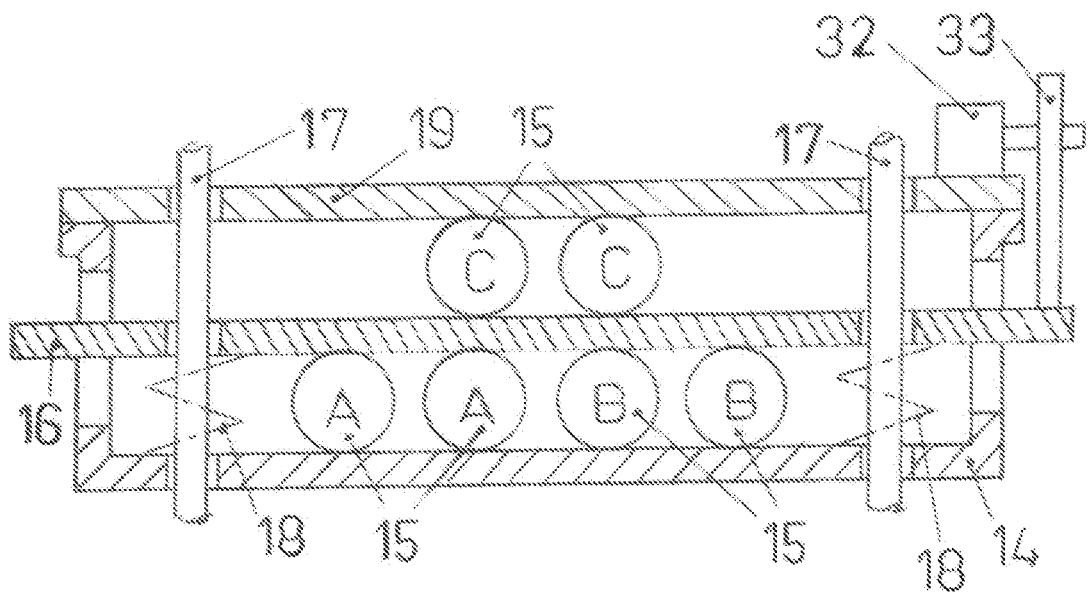
FIG. 3D shows simplified schematic of the First Alternative of the Powered Inhalation-Exhalation embodiment of the Active Lung Assist Device.

FIG. 3D shows the best mode of the First Alternative of the Powered Inhalation-Exhalation embodiment of the Active Lung Assist Device.

Figure 4:
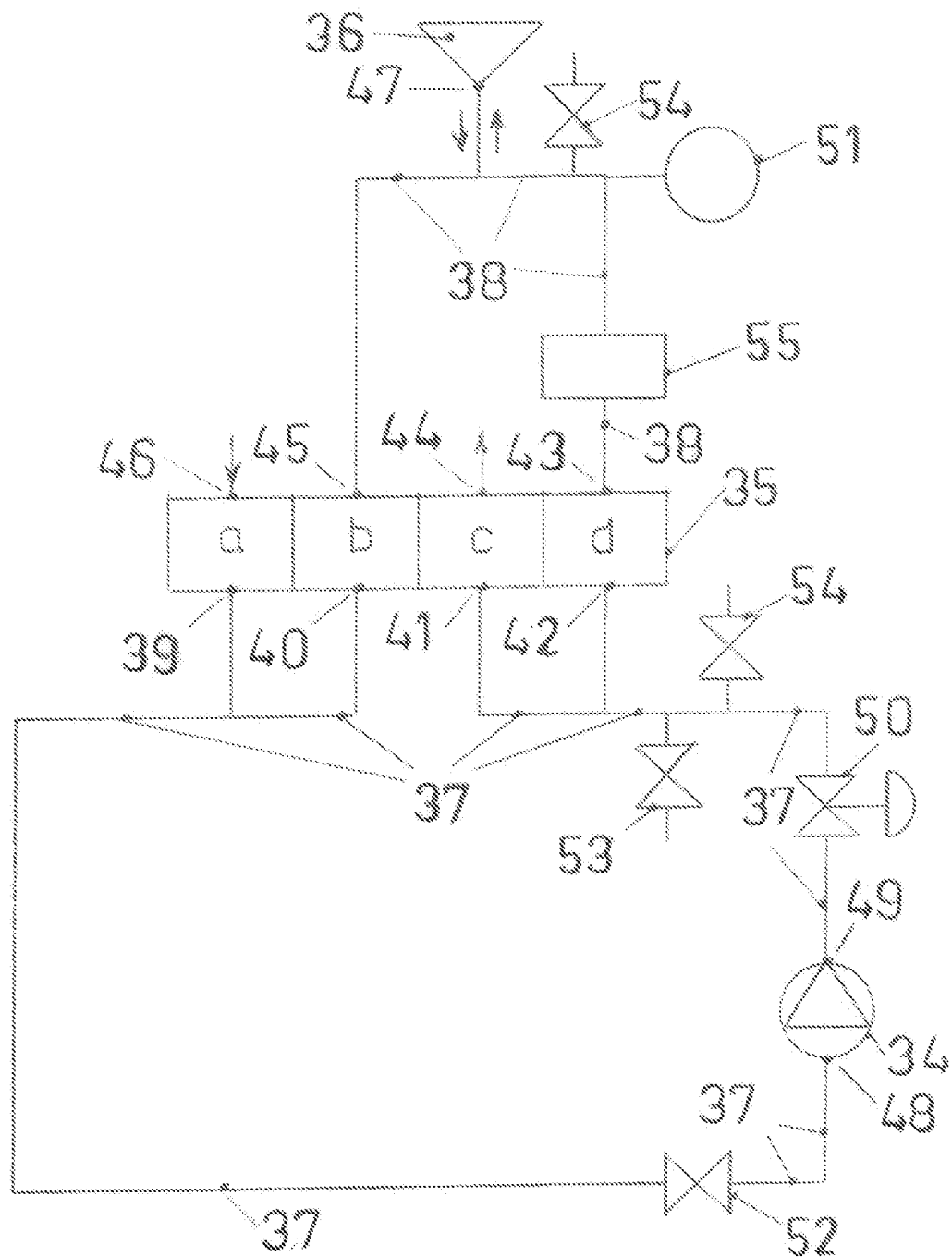
FIG. 4 shows simplified schematic of the Second Alternative of the Powered Inhalation-Exhalation Embodiment of the Active Lung Assist Device.

FIG. 4 shows the best mode of the Second Alternative of the Powered Inhalation-Exhalation Embodiment of the Active Lung Assist Device.

Figure 5:
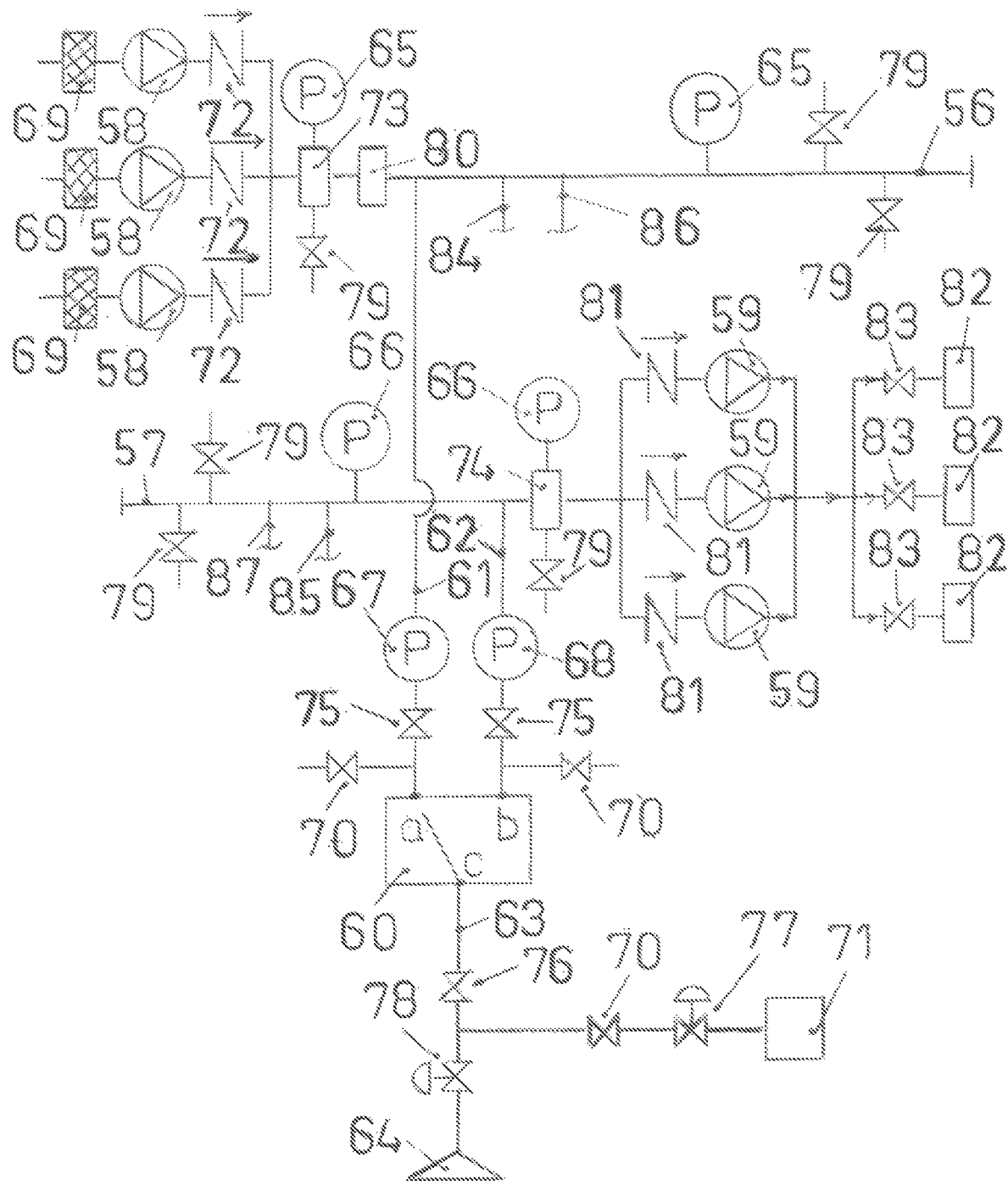
FIG. 5 shows simplified schematic of the Third Alternative of the Powered Inhalation-Exhalation Embodiment of the Active Lung Assist Device.

FIG. 5 shows the best mode of the Third Alternative of the Powered Inhalation-Exhalation Embodiment of the Active Lung Assist Device.

3. General Description of the Manual Exhalation Embodiment of the Active Lung Assist Device The Manual Exhalation embodiment of the Active Lung Assist Device, which is depicted in FIG. 1A and FIG. 1B, can provide assisted exhalation and suctioning of a lung at a desired frequency; its suctioning effect can result in emptying alveoli in a lung from any accumulated fluid or prevent excessive accumulation of fluid within alveoli when the device is used repeatedly over time. This embodiment cannot replace the full functioning of a lung; however, it can prevent fluid accumulation within alveoli in the lung, thus making it possible for the lung to function on its own. This embodiment does not use any powered component; it functions manually.

FIG. 1A shows front view of the Manual Exhalation embodiment of the Active Lung Assist Device; FIG. 1B shows the top view of the Manual Exhalation embodiment of the Active Lung Assist Device.

Referring to FIGS. 1A and 1B, multiple self-inflatable elastic balloons 2, which are connected to each other by a tubing network 3, are laid in a base compartment 1.

Referring to FIGS. 1A and 1B, the compression component 4 is used to squeeze the self-inflatable balloons, thus expelling their internal air content through the open-end point 7 of the tubing network 3. One or multiple number of tube segments of the tubing network 3 may pass through one or multiple openings made in the walls of the base compartment 1 so the open-end point 7 of the tubing network 3 falls outside the base compartment 1. A replaceable mouthpiece might be attached to the end point 7 of tubing network 3 so it can be cleaned or replaced as needed without having to clean the entire Device; the said mouthpiece is not shown in FIGS. 1A and 1B. The openings in the walls of the base compartment 1 are not shown in FIGS. 1A and 1B.

Referring to FIGS. 1A and 1B, one or multiple motion restricting components 5 can be used to control the extent of movement of the compression component 4 and thus prevent damage to those other components that are laid inside the base compartment 1.

Referring to FIGS. 1A and 1B, one or multiple flexible and/or stretchable securing components 6 are used to secure the compression component 4 to the base compartment 1. The securing components 6 can become attached to or detached from either of the base compartment 1 and compression component 4 to allow access to those components that are laid inside the base compartment 1.

FIGS. 1A and 1B show four self-inflatable elastic balloons 2, any other desired number of the said balloons may be used as desired.

FIGS. 1A and 1B show two motion restricting components 5, any other desired number of the said motion restricting components may be used as desired.

FIGS. 1A and 1B show four securing components 6, any other desired number of the said securing components may be used as desired. If balloons 2 are not self-inflatable, then one end of each balloon will be attached and secured to a point on the base compartment 1 and another opposite end of the said balloon is attached and secured to the compression component 4; this will result in forceful inflation of the balloons 2 as the compression component 4 is pulled upward.

4. General Description of the Powered, Non-Automatic, Inhalation-Exhalation Embodiment of the Active Lung Assist Device Referring to FIG. 2, the Powered, Non-Automatic, Inhalation-Exhalation embodiment of the Active Lung Assist Device can provide assisted active inhalation and exhalation to a user patient (thus inflating and suctioning the said lungs) at a desired frequency; its suctioning effect can result in emptying alveoli in the said lungs from any accumulated fluid or prevent excessive accumulation of fluid within alveoli when the device is used repeatedly over time, thus making it possible for the lungs to function on their own in the absence of accumulated fluid within the alveoli.

Referring to FIG. 2, the fluid moving device 8 is equipped with an inlet tube 9 and an outlet tube 10. The fluid moving device 8 may be powered by any type of powering device such as an electric motor, or an internal combustion engine, or any other type of powering device; the powering device of the fluid moving device 8 is not shown in FIG. 2.

Referring to FIG. 2, one end of the vacuum pump inlet tube 9 is connected to the fluid moving device inlet; the other end of the fluid moving device inlet tube 9 is connected to a first wearable breathing compartment 11.

Referring to FIG. 2, one end of the fluid moving device outlet tube 10 is connected to the fluid moving device outlet; the other end of the fluid moving device outlet tube 10 is connected to a second wearable breathing compartment 12.

Referring to FIG. 2, a valve 13 may be included either in the fluid moving device outlet tube 10 or the fluid moving device inlet tube 9 to adjust air pressure and flow rate within the fluid moving device inlet tube 9 or the outlet tube 10. FIG. 2 shows the valve 13 to be mounted in the fluid moving device outlet tube 10.

Referring to FIG. 2, each of the first wearable breathing compartment 11 and the second wearable breathing compartment 12 is equipped with a filtering component; the said filtering components are not shown in FIG. 2.

5. General Description of the Manual Inhalation-Exhalation Embodiment of the Active Lung Assist Device Referring to FIGS. 3A and 3B, the Manual Inhalation-Exhalation embodiment of the Active Lung Assist Device can provide cycles of assisted inhalation and exhalation to a user patient if the device is operated, manually. The inhalation action of the Device supplies atmospheric air to the lungs of the user patient while the exhalation action generates suction from the lungs of the user patient; the suctioning effect can result in emptying alveoli of the lungs of the user patient from any accumulated fluid or prevent excessive accumulation of fluid within the said alveoli when the device is operated for repeated cycles over time.

Referring to FIG. 3A, two sets A and B of the self-inflatable elastic balloons 15 are secured on one side of the compression component 16; a third set C of the self-inflatable elastic balloons 15 are secured on the opposite side of the said compression component 16. The assembly of the three sets A, B, and C of the self-inflatable elastic balloons 15 and the compression component 16 is secured in the base compartment 14. The base compartment 14 has openings on its side surfaces which allow the movement of the compression component 16 with respect to the base compartment 14. The number of the self-inflatable elastic balloons 15 in each of the sets A and B, and their sizes are such that they can provide proper active inhalation and exhalation without having any negative impact on the lungs or function of the lungs of the user patient.

Referring to FIG. 3A, length of the compression component 16 is larger than the length of the base compartment 14, making it possible to apply force to those parts of the compression component 16 that fall outside of the base compartment 14, thus moving the compression component 16 in the side openings of the base compartment 14.

Referring to FIG. 3A, multiple bolts 17, each with its associated nut(s) and washers, are used to tighten the base compartment cover 19 to the base compartment 14. Nut(s) and washers associated with each bolt 17 are not shown in FIG. 3A. Four bolts 17 are used in FIG. 3A; two are seen in the view depicted in FIG. 3A.

Referring to FIG. 3A, one spring 18 is used with each bolt 17; the springs are compressed as the compression component 16 moves downward. Four springs 18 are used in FIG. 3A; two are seen in the view depicted in FIG. 3A. The height of the base compartment 14 is such that when the compression component 16 is pushed downward, it squeezes the balloons 15 of both sets A and B of the self-inflatable elastic balloons completely while allowing all the balloons 15 in the set C of the self-inflatable elastic balloons inflate completely; when the compression component 16 is pushed upward, it squeezes the balloons 15 of the set C of the self-inflatable elastic balloons completely while allowing all the balloons 15 in both sets A and B of the self-inflatable elastic balloons inflate completely.

Referring to FIG. 3A, the compression component 16 may be pushed upward and downward directly or by using a mechanical lever mechanism; the said mechanical lever mechanism is not shown in FIG. 3A.

Referring to FIGS. 3A and 3B, not all components of the Manual Inhalation-Exhalation embodiment of the Active Lung Assist Device are shown in FIG. 3A; tubing networks, check valves, and the wearable breathing compartment 27 are shown only in FIG. 3B.

Referring to FIGS. 3A and 3B, set A of the self-inflatable elastic balloons can comprise any number of balloons 15 as desired; two balloons 15 are shown in the set A of the self-inflatable elastic balloons. Set B of the self-inflatable elastic balloons can comprise any number of balloons 15 as desired; two balloons 15 are shown in the set B of the self-inflatable elastic balloons. Set C of the self-inflatable elastic balloons can comprise any number of balloons 15 as desired; two balloons 15 are shown in the set C of the self-inflatable elastic balloons.

Referring to FIG. 3B, each balloon 15 of the set B of the self-inflatable elastic balloons is connected to the atmospheric air by a check valve 30. At their other ends, the said balloons are connected to the balloons 15 of the set C of the self-inflatable elastic balloons, by the branched tubing network 21.

Referring to FIG. 3B, the tubing network 22 connects the balloons 15 of the set C of the self-inflatable elastic balloons to one port of the check valve 28. The other port of the check valve 28 is connected to the wearable breathing compartment 27 and one port of the check valve 29 by the branched tubing network 23.

Referring to FIG. 3B, the network 24 connects the other port of the check valve 29 to one end of the branched tubing network 25.

Referring to FIG. 3B, each of the balloons 15 of the set A of the self-inflatable elastic balloons is connected to one end of the branched tubing network 25 at one of their ends and to a branched tubing network 26 at their other ends.

Referring to FIG. 3B, one port of each check valve 31 is connected to one end of the branched tubing network 26; the other end of each of the check valves 31 is open to the atmospheric air. The direction of flow for each check valve is shown in FIG. 3B.

Referring to FIGS. 3B and 3C, branched tubing network 20 is a tubing network with multiple ends; each end can be connected to another component of the Active Lung Assist Device. FIG. 3B shows two branched tubing networks 20, each connecting a balloon B to a check valve 30. FIG. 3C shows a branched tubing network 20 connecting two balloons B to a check valve 30. The other ends of the said check valves are open to atmospheric air.

Referring to FIGS. 3B and 3C, branched tubing network 26 is a tubing network with multiple ends; each end can be connected to another component of the Active Lung Assist Device. FIG. 3B shows two branched tubing networks 26, each connecting a balloon A to a check valve 31. FIG. 3C shows a branched tubing network 26 connecting two balloons A to a check valve 31. The other ends of the said check valves are open to atmospheric air.

Referring to FIGS. 3A, 3B, and 3C, if balloons 15 are not self-inflatable, then one end of each balloon will be attached and secured to a fixed component such as either the base compartment 14 or the base compartment cover 19 and their opposite ends are attached and secured to the compression component 16; this will result in forceful inflation of the said balloons 15 as one of their ends is pulled by the compression component 16.

Referring to FIGS. 3B and 3C, the wearable breathing compartment 27 is equipped with a filtering component; the said filtering component is not shown in any of the FIGS. 3B and 3C.

6. General Description of the First Alternative of the Powered Inhalation-Exhalation Embodiment of the Active Lung Assist Device Referring to FIG. 3D, the First Alternative of the Powered Inhalation-Exhalation Embodiment of the Active Lung Assist Device, is different from the Manual Inhalation-Exhalation embodiment of the Active Lung Assist Device in which the alternating upward and downward movements of the compression component 16 is caused by an electric motor and a cam which converts the rotational motion of the shaft of the electric motor to the alternating upward and downward movements of the compression component 16. The detailed sketches that are shown in FIGS. 3B and 3C also apply to the First Alternative of the Powered Inhalation-Exhalation Embodiment of the Active Lung Assist Device that is shown in FIG. 3D.

Referring to FIG. 3D, an electric motor 32 is mounted on the base compartment cover 19 with a cam 33, that is used as the motion conversion mechanism, mounted on the shaft of the said electric motor; the cam 33 is kept in contact with the compression component 16.

Referring to FIG. 3D, as the shaft of the electric motor 32 rotates, the cam 33 is rotated with it, thus makes the compression component 16 move upward and downward alternatingly. Equivalently, the electric motor 32 can be mounted on the base compartment 14, if desired.

Referring to FIG. 3D, if balloons 15 are not self-inflatable, then one end of each balloon will be attached and secured to a fixed component such as either the base compartment 14 or the base compartment cover 19 and their opposite ends are attached and secured to the compression component 16; this will result in forceful inflation of the said balloons 15 as one of their ends is pulled by the compression component 16.

7. General Description of the Second Alternative of the Powered Inhalation-Exhalation Embodiment of the Active Lung Assist Device Referring to FIG. 4, the Second Alternative of the Powered Inhalation-Exhalation Embodiment of the Active Lung Assist Device comprises a fluid moving device 34, a directional valve 35, a wearable breathing compartment 36, a primary branched tubing network 37, a secondary branched tubing network 38, a control valve 50 to control pressure and/or flow rate in the primary branched tubing network 37, a function monitoring system 51 to show that the Active lung Assist Device is functioning properly in supplying breathable air to the wearable breathing compartment 36; the function monitoring system 51 can be as simple as an elastic inflatable component or it can also comprise one or multiple computerized components to monitor and control various respiratory parameters of the user patient, multiple valves 52 each at a different part of the primary branched tubing network 37 and the secondary branched tubing network 38 to isolate different parts of the Device from each other when needed, multiple drain valves 53 each at a different part of the primary branched tubing network 37 and the secondary branched tubing network 38, multiple vent valves 54 each at a different part of the primary branched tubing network 37 and the secondary branched tubing network 38, a conditioning unit 55 for the pressurized air to assure that quality breathable air is supplied to the wearable breathing compartment 36 and the user patient. Components of the Active Lung Assist Device may be mounted on a base structure that might be equipped with wheels; the said base structure and its wheels are not shown in FIG. 4.

Referring to FIG. 4, the directional valve 35 may be equipped with any type of electrical or pneumatic actuator; the actuator is not shown in FIG. 4. The directional valve 35 can have multiple internal channels and ports; FIG. 4 shows a directional valve 35 with four internal channels and eight ports.

Referring to FIG. 4, upon activation of the directional valve 35 by its actuator, each internal channel may become open or closed to the fluid flow. Each channel connects two ports of the directional valve 35 as the followings:

Channel a: connects Ports 39 and 46.
Channel b: connects Ports 40 and 45.
Channel c: connects Ports 41 and 44.
Channel d: connects Ports 42 and 43.

Referring to FIG. 4, one end point of the primary branched tubing network 37 is connected to port 48, inlet of the fluid moving device 34. Another end point of the primary branched tubing network 37 is connected to port 49, outlet of the fluid moving device 34. Each of the other four end points of the primary branched tubing network 37 are each connected to one of the ports 39, 40, 41, or 42 of the directional valve 35.

Referring to FIG. 4, one end point of the secondary branched tubing network 38 is connected to port 47 of the wearable breathing compartment 36; each of the other two end points of secondary branched tubing network 38 are each connected to one of the ports 43 and 45 of the directional valve 35. Ports 44 and 46 are both open to atmospheric air.

Referring to FIG. 4, ports 44 and 46 of the directional valve 35 as well as the wearable breathing compartment 36 may be equipped with air filtering components; the said air filtering components are not shown in FIG. 4.

8. General Description of the Third Alternative of the Powered Inhalation-Exhalation Embodiment of the Active Lung Assist Device Referring to FIG. 5, the Third Alternative of the Powered Inhalation-Exhalation Embodiment of the Active Lung Assist Device can provide active inhalation and exhalation to mass users simultaneously, thus it can be used in hospitals, or in emergency medical installations to combat pandemic respiratory disease crises.

Referring to FIG. 5, the Third Alternative of the Powered Inhalation-Exhalation Embodiment of the Active Lung Assist Device comprises a pressurized compartment 56 containing pressurized breathable air or oxygen.

Referring to FIG. 5, the Third Alternative of the Powered Inhalation-Exhalation Embodiment of the Active Lung Assist Device comprises at least one fluid moving device 58 to pressurize a source of available breathable air or oxygen and provide the pressurized air or oxygen to the pressurized compartment 56.

Referring to FIG. 5, the Third Alternative of the Powered Inhalation-Exhalation Embodiment of the Active Lung Assist Device comprises any type of pneumatic or mechanical or electrical device or any combination of them that can provide a driving force for each fluid moving device 58 (not shown on FIG. 5).

Referring to FIG. 5, the Third Alternative of the Powered Inhalation-Exhalation Embodiment of the Active Lung Assist Device comprises a vacuum compartment 57 which can hold a vacuum within it.

Referring to FIG. 5, the Third Alternative of the Powered Inhalation-Exhalation Embodiment of the Active Lung Assist Device comprises at least one fluid moving device 59 to generate a vacuum in the vacuum compartment 57.

Referring to FIG. 5, the Third Alternative of the Powered Inhalation-Exhalation Embodiment of the Active Lung Assist Device comprises any type of pneumatic or mechanical or electrical device or any combination of them that can provide power to each fluid moving device 59 (not shown on FIG. 5).

Referring to FIG. 5, the Third Alternative of the Powered Inhalation-Exhalation Embodiment of the Active Lung Assist Device comprises at least one directional valve 60 with multiple inlet and exit ports in which two ports can become internally connected to each other or disconnected from each other in sequences, thus allowing gaseous and/or non-gaseous substances enter and exit the directional valve 60 in sequences. One port of the directional valve 60 is in connection with the pressurized compartment 56; another port of the directional valve 60 is in connection with the vacuum compartment 57.

Referring to FIG. 5, the Third Alternative of the Powered Inhalation-Exhalation Embodiment of the Active Lung Assist Device comprises any type of pneumatic or mechanical or electrical actuator or any combination of those actuators that can provide a driving force to each directional valve 60 to connect or disconnect two of its ports to each other or from each other alternatingly and for an adjustable preset time interval so the mentioned ports can remain connected to each other or disconnected from each other alternatingly and for an adjustable preset time interval to accommodate respiratory needs of each user patient that uses the wearable breathing compartment 64. Actuator is not shown on FIG. 5.

Referring to FIG. 5, the Third Alternative of the Powered Inhalation-Exhalation Embodiment of the Active Lung Assist Device comprises a fluid passing conduit 61 that connects one point of the pressurized compartment 56 to port a of the directional valve 60.

Referring to FIG. 5, the Third Alternative of the Powered Inhalation-Exhalation Embodiment of the Active Lung Assist Device comprises at least one fluid passing conduit 62 that connects one point of the vacuum compartment 57 to port b of the directional valve 60.

Referring to FIG. 5, the Third Alternative of the Powered Inhalation-Exhalation Embodiment of the Active Lung Assist Device comprises at least one branched tubing network 63, with one of its ends connected to port c of the directional valve 60. Another end of the branched tubing network 63 is connected to a wearable breathing compartment 64. The wearable breathing compartment 64 may be equipped with an air filtering component; the said air filtering component is not shown in FIG. 5. A third end of the branched tubing network 63 is attached to a function monitoring system 71 to show that the Active lung Assist Device is functioning properly. The function monitoring system 71 can be as simple as an elastic inflatable component; it can also comprise one or multiple computerized components to monitor and control various respiratory and cardiac parameters. The wearable breathing compartment 64 provides active exhalation and inhalation to a patient who wears the wearable breathing compartment 64.

Referring to FIG. 5, each pressure regulation system 65 of the Third Alternative of the Powered Inhalation-Exhalation Embodiment of the Active Lung Assist Device is comprised of multiple components that combined can monitor and maintain a preset adjustable positive pressure within the pressurized compartment 56 and the pressurized fluctuation minimization tank 73.

Referring to FIG. 5, each pressure regulation system 66 of the Third Alternative of the Powered Inhalation-Exhalation Embodiment of the Active Lung Assist Device is comprised of multiple components that combined can monitor and maintain a preset adjustable vacuum pressure within the vacuum compartment 57 or the vacuum fluctuation minimization tank 74.

Referring to FIG. 5, the pressure regulation system 67 of the Third Alternative of the Powered Inhalation-Exhalation Embodiment of the Active Lung Assist Device is comprised of multiple components that combined can monitor and maintain a preset adjustable positive pressure within the fluid passing conduit 61 at its connection to the directional valve 60 so breathable air or oxygen with adjustable pressure and flow rate can be supplied to the directional valve 60.

Referring to FIG. 5, the pressure regulation system 68 of the Third Alternative of the Powered Inhalation-Exhalation Embodiment of the Active Lung Assist Device is comprised of multiple components that combined can monitor and maintain a preset adjustable vacuum pressure within the fluid passing conduit 62 at its connection to the directional valve 60.

Referring to FIG. 5, the Third Alternative of the Powered Inhalation-Exhalation Embodiment of the Active Lung Assist Device comprises at least one filtering component 69 to prevent airborne biohazard and particulate substances from entering component 58 or 56.

Referring to FIG. 5, the Third Alternative of the Powered Inhalation-Exhalation Embodiment of the Active Lung Assist Device comprises multiple valves 70 to isolate one component of the Active lung Assist Device from some other components of the Device, or allow injection and draining disinfecting fluids into and from the Device used for in situ disinfection of a desired portion of the Active lung Assist Device internally.

Referring to FIG. 5, the Third Alternative of the Powered Inhalation-Exhalation Embodiment of the Active Lung Assist Device comprises a function monitoring system 71 to show that the Active lung Assist Device is functioning properly in supplying breathable air or oxygen to the wearable breathing compartment 64. The function monitoring system 71 can be as simple as an elastic inflatable component; it can also comprise one or multiple computerized components to monitor and control various respiratory and cardiac parameters.

Referring to FIG. 5, the Third Alternative of the Powered Inhalation-Exhalation Embodiment of the Active Lung Assist Device comprises multiple check valves 72, each mounted in a tube segment in the pressurized side of the Active lung Assist Device to allow flow of fluid in that segment only in one direction.

Referring to FIG. 5, the Third Alternative of the Powered Inhalation-Exhalation Embodiment of the Active Lung Assist Device comprises a pressurized fluctuation minimization tank 73 to hold pressurized air or oxygen so it can minimize pressure fluctuation in the pressurized compartment 56 or other components of the Active lung Assist Device that receive pressurized air from the pressurized compartment 56.

Referring to FIG. 5, the Third Alternative of the Powered Inhalation-Exhalation Embodiment of the Active Lung Assist Device comprises a vacuum fluctuation minimization tank 74 to minimize fluctuation of vacuum pressure in the vacuum compartment 57 or other components of the Active lung Assist Device that are maintained under a vacuum pressure.

Referring to FIG. 5, the Third Alternative of the Powered Inhalation-Exhalation Embodiment of the Active Lung Assist Device comprises multiple valves 75 to adjust flow rate to or from the directional valve 60 or disconnect and separate some components of the Active lung Assist Device from the rest of its components for cleaning and disinfection as needed.

Referring to FIG. 5, the Third Alternative of the Powered Inhalation-Exhalation Embodiment of the Active Lung Assist Device comprises multiple valves 76 to adjust flow rate to or from the wearable breathing compartment 64 and the function monitoring system 71.

Referring to FIG. 5, the Third Alternative of the Powered Inhalation-Exhalation Embodiment of the Active Lung Assist Device comprises at least one control valve 77 that is normally open but closes to isolate the function monitoring system 71 from the rest of the components of the Active lung Assist Device if the function monitoring system 71 has significant and continued leak or does not function properly, so other components of the Active lung Assist Device can continue to function and generate proper positive pressure or vacuum within the wearable breathing compartment 64.

Referring to FIG. 5, the Third Alternative of the Powered Inhalation-Exhalation Embodiment of the Active Lung Assist Device comprises at least one directional control valve 78 that normally connects the wearable breathing compartment 64 to other components of the Active lung Assist Device. If the wearable breathing compartment 64 does not function properly or sufficient pressurized and conditioned air or oxygen is not supplied to the wearable breathing compartment 64, the directional control valve 78 isolates the wearable breathing compartment 64 from the rest of the components of the Active lung Assist Device and connects it to the atmospheric air instead to prevent suffocation of the patient that is using the wearable breathing compartment 64. The port of the directional control valve 78 that connects the wearable breathing compartment 64 to the atmospheric air is not shown in FIG. 5.

Referring to FIG. 5, the Third Alternative of the Powered Inhalation-Exhalation Embodiment of the Active Lung Assist Device comprises a desired number of valves 79 used to drain and/or vent any tubing segment or component of the Active lung Assist Device. Not all drain and/or vent valves are shown in FIG. 5.

Referring to FIG. 5, the Third Alternative of the Powered Inhalation-Exhalation Embodiment of the Active Lung Assist Device comprises a conditioning unit 80 for the pressurized air or oxygen to assure that quality breathable air or oxygen is supplied to the user patient.

Referring to FIG. 5, the Third Alternative of the Powered Inhalation-Exhalation Embodiment of the Active Lung Assist Device comprises a desired number of check valves 81, each mounted in a tube segment in the vacuum side of the Active lung Assist Device to allow flow of fluid in that segment only in one direction.

Referring to FIG. 5, the Third Alternative of the Powered Inhalation-Exhalation Embodiment of the Active Lung Assist Device comprises a desired number of biohazard collection tanks 82 in which the substances that are expelled through exhalation or coughs of the patients, which are supported by the Active lung Assist Device, are stored.

Referring to FIG. 5, the Third Alternative of the Powered Inhalation-Exhalation Embodiment of the Active Lung Assist Device comprises an isolating valve 83 for each biohazard collection tank 82 to disconnect the biohazard collection tank 82 from the rest of the components of the Active lung Assist Device for maintenance operations or disposal of its stored biohazard substances.

Referring to FIG. 5, the Third Alternative of the Powered Inhalation-Exhalation Embodiment of the Active Lung Assist Device comprises a fluid passing conduit 84 that connects a second point of the pressurized compartment 56 to port a of a second directional valve 60. Also, a fluid passing conduit 85 that connects a second point of the vacuum compartment 57 to port b of the second directional valve 60; the fluid passing conduits 84 and 85 and their associated components, up to the second wearable breathing compartment, are used to serve a second user patient, simultaneously. The second directional valve 60 and its associated components are not shown in FIG. 5.

Referring to FIG. 5, the Third Alternative of the Powered Inhalation-Exhalation Embodiment of the Active Lung Assist Device comprises a fluid passing conduit 86 that connects a third point of the pressurized compartment 56 to port a of a third directional valve 60. Also, a fluid passing conduit 87 that connects a third point of the vacuum compartment 57 to port b of the third directional valve 60; the fluid passing conduits 86 and 87 and their associated components, up to the third wearable breathing compartment, are used to serve a third user patient, simultaneously. The third directional valve 60 and its associated components are not shown in FIG. 5.

Referring to FIG. 5, the Third Alternative of the Powered Inhalation-Exhalation Embodiment of the Active Lung Assist Device comprises any desired number of additional sets, each set comprised of directional valves 60 and their associated components, up to the pressurized compartment 56 and the vacuum compartment 57 at one end and up to a wearable breathing compartment at the other end, that can be used to serve additional user patients, simultaneously. The said additional sets are not shown in FIG. 5.

Referring to FIG. 5, the Third Alternative of the Powered Inhalation-Exhalation Embodiment of the Active Lung Assist Device has a pressurized side and a vacuum side. The directional valve 60 connects the wearable breathing compartment 64 to either the pressurized side or the vacuum side of the Device alternatingly, thus it provides pressurized air or oxygen to the user patient for active inhalation, or it provides suction for active exhalation. The Device can provide a quick relief in pandemic respiratory disease crises, as well as in other respiratory disorders in which lungs cannot function on their own, because of accumulation of excessive fluid in lungs' air sacs (alveoli), by suctioning the accumulated fluid in the lungs in a short time and thus enable the lungs to resume their gas exchange functionality on their own in a short time.

9. How to Make the Manual Exhalation Embodiment of the Active Lung Assist Device Referring to FIGS. 1A and 1B, the base compartment 1 is a cubical space with the top side open; it has holes on at least one of its side walls so tubing can pass through the said holes as required. The base compartment 1 can be built as a single part or assembly of multiple parts connected to each other by use of threaded features, bolts, nuts and washers, U-bolts, screws, pivots, rivets, pins, retaining rings, clamps, hinges, any type of adjustable quick tie strap, any type of twist tie, any type of cable tie, any type of fasteners, welding, soldering, adhesives, thermal fitting, press fitting, Snap-on features, spindles, or any combination of the above said means. The base compartment 1 can have any desired dimensions and can be made from metal or non-metal materials, or a combination of metal and non-metal materials.

Referring to FIGS. 1A and 1B, the self-inflatable elastic balloon 2 is a shell that is built with rubber or any other elastic material; it has at least one opening on its surface to allow fluid flow into the shell or out of the shell when it is squeezed or released. Balloon 2 can be self-inflatable or become inflated by the action of one or more other components of the Manual Exhalation embodiment of the Active Lung Assist Device. Balloon 2 can have any desired shape, geometry, and dimensions. Tubing can be connected to the openings of the balloon 2 by use of threaded features, bolts, nuts, and washers, screws, adhesives, clamps, press fitting, flanged or Snap-on features, or any combination of the above said means.

Referring to FIGS. 1A and 1B, the tubing network 3, is a branched tubing network with multiple ends; it can be built with tubbing segments, with any material or combination of materials, that are connected to each other by fittings. One end of the tubing network 3 is open to atmospheric air; the other ends are each connected to the opening of a balloon 2.

Referring to FIGS. 1A and 1B, the compression component 4 is a flat part with outside dimensions such that it can slide within the base compartment 1, freely, between the bottom and the top open side of the base compartment 1. The compression component 4 can be made from metal or non-metal materials, or a combination of metal and non-metal materials. The compression component 4 can be built as a single part or assembly of multiple parts connected to each other using threaded features, bolts, nuts and washers, screws, pivots, rivets, pins, retaining rings, hinges, welding, soldering, adhesives, thermal fitting, press fitting, Snap-on features, or any combination of the above said means.

Referring to FIGS. 1A and 1B, the motion restricting component 5 is a cylindrical component and is attached to the base compartment 1 along one of its internal edges to limit the downward movement of the compression component 4. The motion restricting component 5 can be made from metal or non-metal materials, or a combination of metal and non-metal materials. The motion restricting component 5 can be attached to the base compartment 1 by bolts, nuts and washers, screws, pivots, rivets, pins, retaining rings, welding, soldering, adhesives, thermal fitting, press fitting, Snap-on features, or any combination of the above said means.

Referring to FIGS. 1A and 1B, the securing component 6 can be made from rigid or flexible materials, it is attached to the base compartment 1 at one of its ends and to the compression component 4 at its other end. The securing component 6 can be attached to the base compartment 1 and the compression component 4 by bolts, nuts and washers, screws, pivots, rivets, pins, retaining rings, welding, soldering, adhesives, thermal fitting, press fitting, Snap-on features, or any combination of the above said means.

10. How to Make the Powered, Non-Automatic, Inhalation-Exhalation Embodiment of the Active Lung Assist Device Referring to FIG. 2, the fluid moving device 8 can be either a compressor or a vacuum pump, as desired, with an inlet port and an exit port; tubing can be connected to either of the said ports by threaded features, bolts and nuts, flanges, press fitting, Snap-on features, clamps, or any type of quick release fitting and couplings.

Referring to FIG. 2, the fluid moving device inlet tube 9 is a tubing network that connects the fluid moving device 8 to the first wearable breathing compartment 11. The fluid moving device inlet tube 9 can be with any rigid or flexible material; it can be connected to either the fluid moving device 8 or the first wearable breathing compartment 11 by threaded features, bolts and nuts, flanges, press fitting, Snap-on features, clamps, or any type of quick release fitting and couplings.

Referring to FIG. 2, the fluid moving device outlet tube 10 is a tubing network that connects the fluid moving device 8 to the second wearable breathing compartment 12. The fluid moving device outlet tube 10 includes at least one valve for adjusting flow rate and/or the pressure of the fluid that is flowing through the fluid moving device outlet tube 10. The fluid moving device outlet tube 10 can be made with any rigid or flexible material; it can be connected to other components of the Powered, Non-Automatic, Inhalation-Exhalation embodiment of the Active Lung Assist Device by threaded features, bolts and nuts, flanges, press fitting, Snap-on features, clamps, or any type of quick release fitting and couplings.

Referring to FIG. 2, the first wearable breathing compartment 11 is a mask that can be mounted and secured on the face of a user patient to cover the nose and mouth of the said user and seal the said nose and mouth from atmospheric air. Similarly, the first wearable breathing compartment 11 might be mounted on the shoulders or around the neck to seal the entire head, face, and neck of the user patient from the atmospheric air. The first wearable breathing compartment 11 can be built from metal or non-metal materials or combination of materials so that it has sufficient strength to maintain its integrity when it is subjected to a vacuum pressure.

Referring to FIG. 2, the second wearable breathing compartment 12 is a mask that can be mounted and secured on the face of a user patient to cover the nose and mouth of the said user and seal the said nose and mouth from atmospheric air. Similarly, the second wearable breathing compartment 12 might be mounted on the shoulders or around the neck to seal the entire head, face, and neck of the user patient from the atmospheric air. The second wearable breathing compartment 12 can be built from metal or non-metal materials or combination of materials so that it has sufficient strength to maintain its integrity when it is subjected to a vacuum pressure.

Referring to FIG. 2, the valve 13 can be any type of valve that is used to adjust flow rate and pressure within the fluid moving device outlet tube 10; it can be connected to other components by threaded features, bolts and nuts, flanges, press fitting, Snap-on features, clamps, or any type of quick release fitting and couplings.

11. How to Make the Manual Inhalation-Exhalation and the First Alternative of the Powered Inhalation-Exhalation Embodiment of the Active Lung Assist Device Referring to FIGS. 3A and 3B, the base compartment 14 is a cubical space with the top side open; it has openings on its side walls so tubing can pass through the said openings as required; it also has openings on two of its opposite side walls to allow upward-downward movements of the compression component 16 through the said openings. Additionally, the base compartment 14 has openings on its bottom side to allow passage of the bolts 17. The side walls of the base compartment 14 extend horizontally to provide a seat for mounting the base compartment cover 19 on the base compartment 14. The base compartment 14 can be built as a single part or assembly of multiple parts connected to each other by use of threaded features, bolts, nuts and washers, U-bolts, screws, pivots, rivets, pins, retaining rings, clamps, hinges, any type of adjustable quick tie strap, any type of twist tie, any type of cable tie, any type of fasteners, welding, soldering, adhesives, thermal fitting, press fitting, Snap-on features, spindles, or any combination of the above said means. The base compartment 14 can have any desired dimensions and can be made from metal or non-metal materials, or a combination of metal and non-metal materials. There are openings on the horizontally extended surfaces of the side walls base compartment 14 to accommodate passage of fasteners through the said openings.

Referring to FIGS. 3A, 3B, 3C, and 3D, the self-inflatable elastic balloon 15 is a shell that is built with rubber or any other elastic material; it has two openings on its surface to allow fluid flow into the shell or out of the shell when it is squeezed or released. Balloon 15 can be self-inflatable or become inflated by the action of one or more other components of the Manual Inhalation-Exhalation or the First Alternative of the Powered Inhalation-Exhalation Embodiment of the Active Lung Assist Device. Balloon 15 can have any desired shape, geometry, and dimensions. Tubing can be connected to the openings of the balloon 15 by use of threaded features, bolts, nuts, and washers, screws, adhesives, clamps, press fitting, flanged or Snap-on features, or any combination of the above said means.

Referring to FIGS. 3A and 3D, the compression component 16 is a flat part with holes on it for the passage of the bolts 17; the compression component 16 can be made from metal or non-metal materials, or a combination of metal and non-metal materials. The compression component 16 can be built as a single part or assembly of multiple parts connected to each other using threaded features, bolts, nuts and washers, screws, pivots, rivets, pins, retaining rings, hinges, welding, soldering, adhesives, thermal fitting, press fitting, Snap-on features, or any combination of the above said means.

Referring to FIGS. 3A and 3D, the bolt 17 is any type of bolt, it is used with at least one nut and one washer. The bolt 17 can have any desired dimensions and can be made from metal or non-metal materials.

Referring to FIGS. 3A and 3D, spring 18 can be any type of compression spring with any size and dimensions; it brings the compression component 16 back to its initial position after the said compression component has been made to move upward or downward with respect to its initial position. Each bolt 17 passes through a spring 18. One end of the spring 18 is in contact with the compression component 16 and its other end is in contact with the base compartment 14.

Referring to FIGS. 3A and 3D, the base compartment cover 19 is a flat part with holes on it for the passage of the bolts 17; the base compartment cover 19 can be made from metal or non-metal materials, or a combination of metal and non-metal materials. The base compartment cover 19 can be built as a single part or assembly of multiple parts connected to each other using threaded features, bolts, nuts and washers, screws, pivots, rivets, pins, retaining rings, hinges, welding, soldering, adhesives, thermal fitting, press fitting, Snap-on features, or any combination of the above said means. The base compartment cover 19 has holes on it so it be attached to the base compartment 14 using any type of fasteners. The base compartment cover 19 also has holes or threaded holes on it for mounting the electric motor 32 on the said base compartment cover.

Referring to FIGS. 3B and 3C, the branched tubing networks 20 is a branched tubing network with multiple ends; it can be built with tubbing segments, with any material or combination of materials, that are connected to each other by fittings. FIG. 3B shows two branched tubing networks 20 each having two ends connecting two components of the Manual Inhalation-Exhalation Embodiment of the Active Lung Assist Device together. FIG. 3C shows one branched tubing networks 20 having three ends connecting three components of the Manual Inhalation-Exhalation Embodiment of the Active Lung Assist Device together.

Referring to FIGS. 3B and 3C, the branched tubing network 21 is a branched tubing network with multiple ends; it can be built with tubbing segments, with any material or combination of materials, that are connected to each other by fittings. FIG. 3B shows one branched tubing network 21 having four ends connecting four components of the Manual Inhalation-Exhalation Embodiment of the Active Lung Assist Device together. FIG. 3C shows one branched tubing network 21 having four ends connecting four components of the Manual Inhalation-Exhalation Embodiment of the Active Lung Assist Device together.

Referring to FIGS. 3B and 3C, the tubing network 22 is a branched tubing network with multiple ends; it can be built with tubbing segments, with any material or combination of materials, that are connected to each other by fittings. FIG. 3B shows one tubing network 22 having three ends connecting three components of the Manual Inhalation-Exhalation Embodiment of the Active Lung Assist Device together. FIG. 3C shows one tubing network 22 having three ends connecting three components of the Manual Inhalation-Exhalation Embodiment of the Active Lung Assist Device together.

Referring to FIGS. 3B and 3C, the branched tubing network 23 is a branched tubing network with multiple ends; it can be built with tubbing segments, with any material or combination of materials, that are connected to each other by fittings. FIG. 3B shows one branched tubing network 23 having three ends connecting three components of the Manual Inhalation-Exhalation Embodiment of the Active Lung Assist Device together. FIG. 3C shows one branched tubing network 23 having three ends connecting three components of the Manual Inhalation-Exhalation Embodiment of the Active Lung Assist Device together.

Referring to FIGS. 3B and 3C, the network 24 is a branched tubing network with multiple ends; it can be built with tubbing segments, with any material or combination of materials, that are connected to each other by fittings. FIG. 3B shows one network 24 having two ends connecting two components of the Manual Inhalation-Exhalation Embodiment of the Active Lung Assist Device together. FIG. 3C shows one network 24 having two ends connecting two components of the Manual Inhalation-Exhalation Embodiment of the Active Lung Assist Device together.

Referring to FIGS. 3B and 3C, the branched tubing network 25 is a branched tubing network with multiple ends; it can be built with tubbing segments, with any material or combination of materials, that are connected to each other by fittings. FIG. 3B shows one branched tubing network 25 having three ends connecting three components of the Manual Inhalation-Exhalation Embodiment of the Active Lung Assist Device together. FIG. 3C shows one branched tubing network 25 having three ends connecting three components of the Manual Inhalation-Exhalation Embodiment of the Active Lung Assist Device together.

Referring to FIGS. 3B and 3C, the branched tubing network 26 is a branched tubing network with multiple ends; it can be built with tubbing segments, with any material or combination of materials, that are connected to each other by fittings. FIG. 3B shows two branched tubing network 26 each having two ends connecting two components of the Manual Inhalation-Exhalation Embodiment of the Active Lung Assist Device together. FIG. 3C shows one branched tubing network 26 having three ends connecting three components of the Manual Inhalation-Exhalation Embodiment of the Active Lung Assist Device together.

Referring to FIGS. 3B and 3C, the wearable breathing compartment 27 is a mask that can be mounted and secured on the face of a user patient to cover the nose and mouth of the said user and seal the said nose and mouth from atmospheric air. Similarly, the wearable breathing compartment 27 might be mounted on the shoulders or around the neck to seal the entire head, face, and neck of the user patient from the atmospheric air. The wearable breathing compartment 27 can be built from metal or non-metal materials or combination of materials so that it has sufficient strength to maintain its integrity when it is subjected to a vacuum pressure.

Referring to FIGS. 3B and 3C, the check valve 28 can be any type of check valve that connects two tubing segments of the Manual Inhalation-Exhalation Embodiment of the Active Lung Assist Device together to maintain fluid flow in one direction through the said tubing segments. The check valve 28 can be connected to the said tubing segments by threaded features, flanges, clamps, press fitting, or any combination of the above said means.

Referring to FIGS. 3B and 3C, the check valve 29 can be any type of check valve that connects two tubing segments of the Manual Inhalation-Exhalation Embodiment of the Active Lung Assist Device together to maintain fluid flow in one direction through the said tubing segments. The check valve 29 can be connected to the said tubing segments by threaded features, flanges, clamps, press fitting, or any combination of the above said means.

Referring to FIGS. 3B and 3C, the check valve 30 can be any type of check valve that is open to atmospheric air at one of its ends and to the branched tubing networks 20 at its other end, to allow flow of atmospheric air into the branched tubing networks 20. The check valve 30 can be connected to the branched tubing networks 20 by threaded features, flanges, clamps, press fitting, or any combination of the above said means.

Referring to FIGS. 3B and 3C, the check valve 31 can be any type of check valve that is open to atmospheric air at one of its ends and is connected to the branched tubing network 26 at its other end, to allow fluid flow from the branched tubing network 26 into the atmospheric air. The check valve 31 can be connected to the branched tubing network 26 by threaded features, flanges, clamps, press fitting, or any combination of the above said means.

Referring to FIG. 3D, the electric motor 32 can be any type of electric motor that can provide a desired rotational speed directly or by inclusion of a rotational speed variation mechanism as needed. The electric motor 32 can be mounted on the base compartment cover 19 by any desired type of fasteners.

Referring to FIG. 3D, the cam 33 is a cam with any desired profile and is mounted on the shaft of the electric motor 32. The cam 33 is also in touch with the compression component 16; rotation of the shaft of the electric motor 32, thus rotation of the cam 33, results in the upward and downward movements of the compression component 16.

12. How to Make the Second Alternative of the Powered Inhalation-Exhalation Embodiment of the Active Lung Assist Device Referring to FIG. 4, the fluid moving device 34 can be any type of compressor or vacuum pump. The inlet port 48 of the fluid moving device 34 is connected to one end of the primary branched tubing network 37 by threaded features, flanges, clamps, press fitting, or any combination of the above said means. Similarly, the outlet port 49 of the fluid moving device 34 is connected to another end of the primary branched tubing network 37 by threaded features, flanges, clamps, press fitting, or any combination of the above said means.

Referring to FIG. 4, the directional valve 35 is a valve with multiple internal, separated canals and with each of the said canals having multiple inlet and exit ports. FIG. 4 shows a directional valve 35 with four internal canals, a, b, c, and d; the said internal canals can become open or closed to fluid flow by the action of the actuator of the said directional valve 35. Port 46 is open to atmosphere, through which breathable air can be taken into the canal a of the directional valve 35. Port 44 is open to atmosphere, through which the fluid contents of the canal c of the directional valve 35 can be expelled out of the said directional valve 35. Ports 39, 40, 41, and 42 are each connected to one of the ends of the primary branched tubing network 37. Ports 43 and 45 are each connected to one of the ends of the secondary branched tubing network 38. The directional valve 35 can have an electrical, or pneumatic, or hydraulic actuator; the said actuator is not shown in FIG. 4. Tubing segments can be connected to the ports of the directional valve 35 by threaded features, flanges, clamps, press fitting, or any combination of the above said means.

Referring to FIG. 4, the wearable breathing compartment 36 is a mask that can be mounted and secured on the face of a user patient to cover the nose and mouth of the said user and seal the said nose and mouth from atmospheric air. Similarly, the wearable breathing compartment 36 might be mounted on the shoulders or around the neck to seal the entire head, face, and neck of the user patient from the atmospheric air. The wearable breathing compartment 36 can be built from metal or non-metal materials or combination of materials so that it has sufficient strength to maintain its integrity when it is subjected to a vacuum pressure. Tubing segments can be connected to the wearable breathing compartment 36 by threaded features, flanges, clamps, press fitting, or any combination of the above said means.

Referring to FIG. 4, the primary branched tubing network 37 is a branched tubing network with multiple ends; it can be built with tubbing segments, with any material or combination of materials and with the said tubing segments being connected to each other directly by fittings, or by being connected to inlet and outlet ports of other components of the Second Alternative of the Powered Inhalation-Exhalation Embodiment of the Active Lung Assist Device. FIG. 4 shows the primary branched tubing network 37 with six ends that are connected to drain valve 53, vent valve 54, and ports 39, 40, 41, and 42 of the directional valve 35. Additionally, some other tubing segments of the primary branched tubing network 37 are also connected to the inlet and outlet ports of the fluid moving device 34, the inlet and outlet ports of the control valve 50, and the inlet and outlet ports of the valve 52.

Referring to FIG. 4, the secondary branched tubing network 38 is a branched tubing network with multiple ends; it can be built with tubbing segments, with any material or combination of materials and with the said tubing segments being connected to each other directly by fittings, or by being connected to inlet and outlet ports of other components of the Second Alternative of the Powered Inhalation-Exhalation Embodiment of the Active Lung Assist Device. FIG. 4 shows the secondary branched tubing network 38 with five ends that are connected to the wearable breathing compartment 36, ports 45 and 43 of the directional valve 35, the vent valve 54, and the function monitoring system 51. Additionally, two other tubing segments of the secondary branched tubing network 38 are also connected to the inlet and outlet ports of the conditioning unit 55.

Referring to FIG. 4, the control valve 50 can be any type of valve, with an actuator, that can be used to control flow rate and fluid pressure within the primary branched tubing network 37. The control valve 50 can have an electrical, or pneumatic, or hydraulic actuator; the said actuator is not shown in FIG. 4. Tubing segments can be connected to the control valve 50 by threaded features, flanges, clamps, press fitting, or any combination of the above said means.

Referring to FIG. 4, the function monitoring system 51 can show that the Active lung Assist Device is functioning properly in supplying breathable air to the wearable breathing compartment 36; the function monitoring system 51 can be as simple as an elastic inflatable component or it can also comprise one or multiple computerized components to monitor and control various respiratory parameters of the user patient. Tubing segments of the Second Alternative of the Powered Inhalation-Exhalation Embodiment of the Active Lung Assist Device can be connected to the function monitoring system 51 by threaded features, flanges, clamps, press fitting, or any combination of the above said means.

Referring to FIG. 4, the valve 52 can be any type of valve that can be used to control flow rate and pressure within the primary branched tubing network 37. Tubing segments of the Second Alternative of the Powered Inhalation-Exhalation Embodiment of the Active Lung Assist Device can be connected to the valve 52 by threaded features, flanges, clamps, press fitting, or any combination of the above said means.

Referring to FIG. 4, the drain valve 53 can be any type of valve that can be used to drain any liquid that might accumulate in the interconnected components and tubing segments of the Second Alternative of the Powered Inhalation-Exhalation Embodiment of the Active Lung Assist Device. Tubing segments of the said embodiment can be connected to the drain valve 53 by threaded features, flanges, clamps, press fitting, or any combination of the above said means.

Referring to FIG. 4, the vent valve 54 can be any type of valve that can be used to vent the interconnected components and tubing segments of the Second Alternative of the Powered Inhalation-Exhalation Embodiment of the Active Lung Assist Device. Tubing segments of the said embodiment can be connected to the vent valve 54 by threaded features, flanges, clamps, press fitting, or any combination of the above said means.

Referring to FIG. 4, the conditioning unit 55 is a unit for adjusting temperature and humidity of the pressurized air to assure that quality breathable air is supplied to the wearable breathing compartment 36 and the user patient. Tubing segments of the Second Alternative of the Powered Inhalation-Exhalation Embodiment of the Active Lung Assist Device can be connected to any port of the conditioning unit 55 by threaded features, flanges, clamps, press fitting, or any combination of the above said means.

Referring to FIG. 4, all components of the Second Alternative of the Powered Inhalation-Exhalation Embodiment of the Active Lung Assist Device can be mounted on a stationary or mobile base structure; the said base structure is not shown in FIG. 4.

13. How to Make the Third Alternative of the Powered Inhalation-Exhalation Embodiment of the Active Lung Assist Device Referring to FIG. 5, the pressurized compartment 56 is a tubular component made with multiple openings to which other components of the Third Alternative of the Powered Inhalation-Exhalation Embodiment of the Active Lung Assist Device can be connected. The pressurized compartment 56 can be built with any materials or combination of materials and with any dimensions and geometry. The pressurized compartment 56 is sealed from the atmospheric air at one of its ends. The pressurized compartment 56 can be built with multiple tubular segments; each segment can be connected to another tubular segment or to another component of the Third Alternative of the Powered Inhalation-Exhalation Embodiment of the Active Lung Assist Device by welding, threaded features, flanges, clamps, press fitting, or any combination of the above said means.

Referring to FIG. 5, the vacuum compartment 57 is a tubular component made with multiple openings to which other components of the Third Alternative of the Powered Inhalation-Exhalation Embodiment of the Active Lung Assist Device can be connected. The vacuum compartment 57 can be built with any materials or combination of materials and with any dimensions and geometry. The vacuum compartment 57 is sealed from the atmospheric air at one of its ends. The vacuum compartment 57 can be built with multiple tubular segments; each segment can be connected to another tubular segment or to another component of the Third Alternative of the Powered Inhalation-Exhalation Embodiment of the Active Lung Assist Device by welding, threaded features, flanges, clamps, press fitting, or any combination of the above said means.

Referring to FIG. 5, the fluid moving device 58 can be any type of compressor or vacuum pump. The inlet port of the fluid moving device 58 can be connected to the outlet port of the filtering component 69 by threaded features, flanges, clamps, press fitting, or any combination of the above said means. Similarly, the outlet port of the fluid moving device 58 can be connected to the inlet port of the check valve 72 by threaded features, flanges, clamps, press fitting, or any combination of the above said means.

Referring to FIG. 5, the fluid moving device 59 can be any type of compressor or vacuum pump. The inlet port of the fluid moving device 59 can be connected to the outlet port of the check valve 81 by threaded features, flanges, clamps, press fitting, or any combination of the above said means. Similarly, the outlet port of the fluid moving device 59 can be connected to the inlet port of the isolating valve 83 by tubular segments and using threaded features, flanges, clamps, press fitting, or any combination of the above said means.

Referring to FIG. 5, the directional valve 60 can be a valve with multiple internal, separated canals and with each of the said canals having its inlet and exit ports. FIG. 5 shows a directional valve 60 with two internal canals and three ports a, b, and c. By the action of the actuator of the directional valve 60, port c can become connected to either port a or port b. The directional valve 60 can have an electrical, or pneumatic, or hydraulic actuator; the said actuator is not shown in FIG. 5. Tubing segments can be connected to the ports of the directional valve 60 by threaded features, flanges, clamps, press fitting, or any combination of the above said means.

Referring to FIG. 5, the fluid passing conduit 61 is a tubular segment, or combination of tubular segments connected to each other, which connects two components of the Third Alternative of the Powered Inhalation-Exhalation Embodiment of the Active Lung Assist Device together. The fluid passing conduit 61 can be built with any material or combination of materials and with any dimensions and geometry. The fluid passing conduit 61 can be connected to other components of the said embodiment by threaded features, flanges, clamps, press fitting, or any combination of the above said means. FIG. 5 shows the fluid passing conduit 61 connecting one opening of the pressurized compartment 56 to a pressure regulation system 67.

Referring to FIG. 5, the fluid passing conduit 62 is a tubular segment, or combination of tubular segments connected to each other, which connects two components of the Third Alternative of the Powered Inhalation-Exhalation Embodiment of the Active Lung Assist Device together. The fluid passing conduit 62 can be built with any material or combination of materials and with any dimensions and geometry. The fluid passing conduit 62 can be connected to other components of the said embodiment by threaded features, flanges, clamps, press fitting, or any combination of the above said means. FIG. 5 shows the fluid passing conduit 62 connecting one opening of the vacuum compartment 57 to a pressure regulation system 68.

Referring to FIG. 5, the branched tubing network 63 is a tubing network with multiple ends; it can be built with tubbing segments, with any material or combination of materials and with the said tubing segments being connected to each other directly by fittings, or by being connected to inlet and outlet ports of other components of the Third Alternative of the Powered Inhalation-Exhalation Embodiment of the Active Lung Assist Device. FIG. 5 shows a branched tubing network 63 with three ends that are connected to port c of the directional valve 60, the wearable breathing compartment 64, and the function monitoring system 71. Additionally, some other tubing segments of the branched tubing network 63 are also connected to the inlet and outlet ports of the valve 76, the directional control valve 78, the valve 70, and the control valve 77. The said tubing segments can be connected to the above said components by threaded features, flanges, clamps, press fitting, or any combination of the above said means.

Referring to FIG. 5, the wearable breathing compartment 64 is a mask that can be mounted and secured on the face of a user patient to cover the nose and mouth of the said user and seal the said nose and mouth from atmospheric air. Similarly, the wearable breathing compartment 64 might be mounted on the shoulders or around the neck to seal the entire head, face, and neck of the user patient from the atmospheric air. The wearable breathing compartment 64 can be built from metal or non-metal materials or combination of materials so that it has sufficient strength to maintain its integrity when it is subjected to a vacuum pressure. Tubing segments can be connected to the wearable breathing compartment 64 by threaded features, flanges, clamps, press fitting, or any combination of the above said means.

Referring to FIG. 5, the pressure regulation system 65 is comprised of multiple components that combined can monitor and maintain a preset adjustable positive pressure within the pressurized compartment 56, the pressurized fluctuation minimization tank 73, and any other tubing segments and networks that are connected to the said pressurized compartment 56 or the pressurized fluctuation minimization tank 73.

Referring to FIG. 5, the pressure regulation system 66 is comprised of multiple components that combined can monitor and maintain a preset adjustable vacuum pressure within the vacuum compartment 57, the vacuum fluctuation minimization tank 74, and any other tubing segments and networks that are connected to the said vacuum compartment 57 or the vacuum fluctuation minimization tank 74.

Referring to FIG. 5, the pressure regulation system 67 is comprised of multiple components that combined can monitor and maintain a preset adjustable positive pressure within the fluid passing conduit 61 and any other tubing segments and networks that are connected to the said fluid passing conduit 61.

Referring to FIG. 5, the pressure regulation system 68 is comprised of multiple components that combined can monitor and maintain a preset adjustable vacuum pressure within the fluid passing conduit 62 and any other tubing segments and networks that are connected to the said fluid passing conduit 62.

Referring to FIG. 5, the filtering component 69 can be made from cloth or porous or fibrous material that prevents airborne substances from entering into the fluid moving device 58. The filtering component 69 can be mounted in a duct or on a frame; the said duct or frame are not shown in FIG. 5. The outlet port of the filtering component 69 is connected to the inlet port of the fluid moving device 58.

Referring to FIG. 5, the valve 70 can be any type of valve that can stop fluid flow from one tubular segment to other tubular segments or components of the Third Alternative of the Powered Inhalation-Exhalation Embodiment of the Active Lung Assist Device when the said valve is closed. Tubular segments can be connected to the valve 70 by threaded features, flanges, clamps, press fitting, or any combination of the above said means.

Referring to FIG. 5, the function monitoring system 71 can show that the Third Alternative of the Powered Inhalation-Exhalation Embodiment of the Active Lung Assist Device is functioning properly in supplying breathable air to the wearable breathing compartment 64; the function monitoring system 71 can be as simple as an elastic inflatable component or it can also comprise one or multiple computerized components to monitor and control various respiratory parameters of the user patient. Tubing segments of the Third Alternative of the Powered Inhalation-Exhalation Embodiment of the Active Lung Assist Device can be connected to the function monitoring system 71 by threaded features, flanges, clamps, press fitting, or any combination of the above said means.

Referring to FIG. 5, the check valve 72 can be any type of check valve that connects two tubing segments of the Third Alternative of the Powered Inhalation-Exhalation Embodiment of the Active Lung Assist Device together, to maintain fluid flow in one direction through the said tubing segments. The check valve 72 can be connected to tubing segments by threaded features, flanges, clamps, press fitting, or any combination of the above said means.

Referring to FIG. 5, the pressurized fluctuation minimization tank 73 is a tank that can be built with desired materials or combination of materials and with desired dimensions. The pressurized fluctuation minimization tank 73 serves as a reservoir for the breathable air, thus minimizes pressure fluctuations within the pressurized compartment 56, and other tubular segments and networks that are connected to the said pressurized compartment 56, as the fluid moving device 58 operates or the said breathable air is consumed by user patients. Tubing segments can be connected to the pressurized fluctuation minimization tank 73 by threaded features, flanges, clamps, press fitting, or any combination of the above said means.

Referring to FIG. 5, the vacuum fluctuation minimization tank 74 is a tank that can be built with desired materials or combination of materials and with desired dimensions. The vacuum fluctuation minimization tank 74 serves as a reservoir, which is under vacuum, that minimizes fluctuations in the vacuum pressure within the vacuum compartment 57, and other tubular segments and networks that are connected to the said vacuum compartment 57, as the fluid moving device 59 operates or the exhalation products of the user patients is taken into the vacuum compartment 57 and other tubular segments and networks that are connected to the said vacuum compartment 57. Tubing segments can be connected to the vacuum fluctuation minimization tank 74 by threaded features, flanges, clamps, press fitting, or any combination of the above said means.

Referring to FIG. 5, the valve 75 can be any type of valve that can stop fluid flow from one tubular segment to other tubular segments or components of the Third Alternative of the Powered Inhalation-Exhalation Embodiment of the Active Lung Assist Device when the said valve is closed. Tubular segments can be connected to the valve 75 by threaded features, flanges, clamps, press fitting, or any combination of the above said means.

Referring to FIG. 5, the valve 76 can be any type of valve that can stop fluid flow from one tubular segment to other tubular segments or components of the Third Alternative of the Powered Inhalation-Exhalation Embodiment of the Active Lung Assist Device when the said valve is closed. Tubular segments can be connected to the valve 76 by threaded features, flanges, clamps, press fitting, or any combination of the above said means.

Referring to FIG. 5, the control valve 77 can be any type of valve, with an actuator, that can be used to isolate the function monitoring system 71 from the rest of the components of the Third Alternative of the Powered Inhalation-Exhalation Embodiment of the Active Lung Assist Device if the said function monitoring system 71 has significant and continued leak or does not function properly, so other components of the said embodiment can continue to function and maintain proper positive pressure or vacuum within the wearable breathing compartment 64. The control valve 77 can have an electrical, or pneumatic, or hydraulic actuator; the said actuator is not shown in FIG. 5. Tubing segments can be connected to the control valve 77 by threaded features, flanges, clamps, press fitting, or any combination of the above said means.

Referring to FIG. 5, the directional control valve 78 is a directional valve with two internal canals and three ports; one canal and two of the said ports allow fluid normally to flow from the directional valve 60 towards the wearable breathing compartment 64 and vice versa. As a safety measure, the second canal and the third port of the directional control valve 78 allow the wearable breathing compartment 64 to become connected to atmospheric air if the said wearable breathing compartment 64 does not function properly or if sufficient pressurized and conditioned air or oxygen is not supplied to the wearable breathing compartment 64. The directional control valve 78 can have an electrical, or pneumatic, or hydraulic actuator; the said actuator is not shown in FIG. 5. Tubing segments can be connected to the directional control valve 78 by threaded features, flanges, clamps, press fitting, or any combination of the above said means. The said port of the directional control valve 78 that is open to atmospheric air in not shown in FIG. 5.

Referring to FIG. 5, the valve 79 can be any type of valve that can be used to drain or vent any compartment, or component, or fluid passing conduit of the Third Alternative of the Powered Inhalation-Exhalation Embodiment of the Active Lung Assist Device as desired. Tubular segments can be connected to the valve 79 by threaded features, flanges, clamps, press fitting, or any combination of the above said means.

Referring to FIG. 5, the conditioning unit 80 is a unit for adjusting temperature and humidity of the pressurized air to assure that quality breathable air is supplied to the wearable breathing compartment 64 and the user patient. Tubing segments of the Third Alternative of the Powered Inhalation-Exhalation Embodiment of the Active Lung Assist Device can be connected to any port of the conditioning unit 80 by threaded features, flanges, clamps, press fitting, or any combination of the above said means.

Referring to FIG. 5, the check valve 81 can be any type of check valve that connects two tubing segments of the Third Alternative of the Powered Inhalation-Exhalation Embodiment of the Active Lung Assist Device together, to maintain fluid flow in one direction through the said tubing segments. FIG. 5 shows the check valve 81 to allow fluid flow from the vacuum fluctuation minimization tank 74 towards the fluid moving device 59. The check valve 81 can be connected to tubing segments by threaded features, flanges, clamps, press fitting, or any combination of the above said means.

Referring to FIG. 5, the biohazard collection tank 82 is a storage tank that is used to store exhalation products of the user patients of the Third Alternative of the Powered Inhalation-Exhalation Embodiment of the Active Lung Assist Device, for safe disposal of the said stored exhalation products, as desire. The biohazard collection tank 82 can be made with desired materials or combination of materials and with desired dimensions. Tubular segments can be connected to the biohazard collection tank 82 by threaded features, flanges, clamps, press fitting, or any combination of the above said means.

Referring to FIG. 5, the isolating valve 83 can be any type of valve that can be used to stop fluid flow from one tubular segment to other tubular segments or components of the Third Alternative of the Powered Inhalation-Exhalation Embodiment of the Active Lung Assist Device when the said valve is closed. Tubular segments can be connected to the isolating valve 83 by threaded features, flanges, clamps, press fitting, or any combination of the above said means.

Referring to FIG. 5, the fluid passing conduit 84 is a tubular segment, or combination of tubular segments connected to each other, which is used to supply pressurized breathable air from the pressurized compartment 56 to a second directional valve 60 and a second wearable breathing compartment 64 for a second user patient; the said second directional valve 60 and the second wearable breathing compartment 64, and their associated components, are not shown in FIG. 5. The fluid passing conduit 84 can be built with any material or combination of materials and with any dimensions and geometry. The fluid passing conduit 84 can be connected to other components of the Third Alternative of the Powered Inhalation-Exhalation Embodiment of the Active Lung Assist Device by threaded features, flanges, clamps, press fitting, or any combination of the above said means.

Referring to FIG. 5, the fluid passing conduit 85 is a tubular segment, or combination of tubular segments connected to each other, which is used to connect the vacuum compartment 57 to a second directional valve 60 and a second wearable breathing compartment 64 for a second user patient; the said second directional valve 60 and the second wearable breathing compartment 64, and their associated components, are not shown in FIG. 5. The fluid passing conduit 85 can be built with any material or combination of materials and with any dimensions and geometry. The fluid passing conduit 85 can be connected to other components of the Third Alternative of the Powered Inhalation-Exhalation Embodiment of the Active Lung Assist Device by threaded features, flanges, clamps, press fitting, or any combination of the above said means.

Referring to FIG. 5, the fluid passing conduit 86 is a tubular segment, or combination of tubular segments connected to each other, which is used to supply pressurized breathable air from the pressurized compartment 56 to a third directional valve 60 and a third wearable breathing compartment 64 for a third user patient; the said third directional valve 60 and the third wearable breathing compartment 64, and their associated components, are not shown in FIG. 5. The fluid passing conduit 86 can be built with any material or combination of materials and with any dimensions and geometry. The fluid passing conduit 86 can be connected to other components of the Third Alternative of the Powered Inhalation-Exhalation Embodiment of the Active Lung Assist Device by threaded features, flanges, clamps, press fitting, or any combination of the above said means.

Referring to FIG. 5, the fluid passing conduit 87 is a tubular segment, or combination of tubular segments connected to each other, which is used to connect the vacuum compartment 57 to a third directional valve 60 and a third wearable breathing compartment 64 for a third user patient; the said third directional valve 60 and the third wearable breathing compartment 64, and their associated components, are not shown in FIG. 5. The fluid passing conduit 87 can be built with any material or combination of materials and with any dimensions and geometry. The fluid passing conduit 87 can be connected to other components of the Third Alternative of the Powered Inhalation-Exhalation Embodiment of the Active Lung Assist Device by threaded features, flanges, clamps, press fitting, or any combination of the above said means.

14. Common Instructions on How to Make any Embodiment of the Active Lung Assist Device Any component of any embodiment or alternatives of each embodiment of the Active Lung Assist Device can be built by any type of manufacturing processes such as welding, soldering, casting, die casting, forging, extrusion, sewing, thermal fitting, press fitting, cutting, bending, punching, use of adhesives, Snap-on, or any other existing manufacturing process, or any combination of the said manufacturing processes.

Any component of any embodiment or alternatives of each embodiment of the Active Lung Assist Device can be built as a single part or assembly of multiple parts connected to each other by flanges, use of threaded features, bolts, nuts, and washers, U-bolts, anchor bolts, screws, pivots, rivets, pins, retaining rings, clamps, hangers, hinges, cables, ropes, chains, any type of quick release fitting and couplings, any type of adjustable quick tie strap, any type of twist tie, any type of cable tie, any type of buttons or Snap buttons, any type of zippers, any other type of fasteners, welding, soldering, adhesives, sewing, thermal fitting, press fitting, Snap-on features, magnets, hinges, spindles, any type of springs, any type of ball bearing or sliding bearings, or any combination of the above said means.

Any component of any embodiment or alternatives of each embodiment of the Active Lung Assist Device can be built either as a single component or its combination with one or multiple other components of the said embodiment can be built as a single component.

Any component of any embodiment or alternatives of each embodiment of the Active Lung Assist Device can have any desired shape, geometry, and dimensions and can be made from metal or non-metal materials, or a combination of metal and non-metal materials.

Any component of any embodiment or alternatives of each embodiment of the Active Lung Assist Device can have a uniform cross sectional area or a variable cross sectional area, or a combination of both uniform and variable cross sectional areas as desired.

Any component of any embodiment or alternatives of each embodiment of the Active Lung Assist Device can have a desired number of attachments by which the said component can be lifted for installation or maintenance operations or by which the said component can be mounted on or attached to another component of the said embodiment or to any existing structure; the said attachments are not shown in figures.

Any component of any embodiment or alternatives of each embodiment of the Active Lung Assist Device can be attached to or mounted on another component or structure of the said embodiment or any combination of components and structures of the said embodiment or to any other existing structure by using metal or non-metal or a combination of metal and non-metal structural components, flanges, welding, soldering, bolts, nuts, washers, screws, U-bolts, anchor bolts, use of threaded features, pins, retaining rings, clamps, hangers, hinges, cables, ropes, chains, pivots, rivets, any type of quick release fitting and couplings, any type of adjustable quick tie strap, any type of twist tie, any type of cable tie, any type of buttons or Snap buttons, any type of zippers, any other type of fasteners, sewing, adhesives, thermal fitting, press fitting, Snap-on features, magnets, hinges, spindles, any type of springs, any type of ball bearing or sliding bearings, or any combination of the above said means as desired.

Multiple valves, referred to as isolating valves, can be used at different parts of any embodiment or alternatives of each embodiment to allow removal or isolating any desired component of the said embodiment from the rest of its components for maintenance, trouble shooting, or any other operation as desired. The said isolating valves are not shown in any of the figures.

Any control valve of any embodiment of the Active Lung Assist Device can be activated by an electrical or pneumatic actuator, or a combination of electrical and pneumatic actuators.

Tubing segments of any embodiment of the Active Lung Assist Device can be connected to other components of the said embodiment by threaded features, flanges, clamps, press fitting, or any combination of the above said means.

15. Function of the Manual Exhalation Embodiment of the Active Lung Assist Device Referring to FIGS. 1A and 1B, the compression component 4 is pressed on the self-inflatable elastic balloons 2, resulting in squeezing them thus expelling their internal air content through the open end point 7 of the tubing network 3, or its associated replaceable mouth piece. With the self-inflatable elastic balloons 2 being squeezed, the open end point 7 of the tubing network 3 (or its associated replaceable mouth piece) is placed inside the mouth of the user patient followed by ending squeeze on the self-inflatable elastic balloons 2. This will result in self-inflation of the self-inflatable elastic balloons 2 as they suck out carbon dioxide and other gaseous and non-gaseous contents of the alveoli of the lungs of the user patient. Repeated use of this embodiment over time, as it was discussed above, can prevent fluid accumulation within alveoli of the lungs of the user patient, thus allowing the said lungs keep functioning on their own. The size of the volume of a single self-inflatable elastic balloon 2 and the number of the said balloons is such that the Manual Exhalation embodiment of the Active Lung Assist Device can provide sufficient suctioning power without causing any damage to the alveoli of the lungs of the user patient.

16. Function of the Powered, Non-Automatic, Inhalation-Exhalation Embodiment of the Active Lung Assist Device Referring to FIG. 2, with the first wearable breathing compartment 11 being in use by a user patient, and with the fluid moving device 8 working, the fluid moving device 8 sucks carbon dioxide and other gaseous and non-gaseous contents of the alveoli of the lungs of the user patient. Valve 13 is used to adjust air pressure and flow rate through the vacuum pump inlet tube 9 and the vacuum pump outlet tube 10. Repeated use of this embodiment at a desired frequency, as it was discussed above, can provide active (i.e., forceful) exhalation to the user patient at a desired frequency, thus prevent fluid accumulation within alveoli of the lungs of the said user patient and therefore allowing the said lungs keep functioning on their own in the absence of any accumulated fluid within the alveoli of the said lungs. With the second wearable breathing compartment 12 being in use by the user patient, and with the fluid moving device 8 working, the device can provide active (i.e., forceful) inhalation to the user patient at a desired frequency. The first wearable breathing compartment 11 and the second wearable breathing compartment 12 need to be used by the user patient, alternatingly and with a desired frequency, to receive active inhalation and exhalation at a desired frequency.

17. Function of the Manual Inhalation-Exhalation Embodiment of the Active Lung Assist Device Referring to FIGS. 3A and 3B, when the compression component 16 is pushed downward, all balloons 15 of both sets A and B of the self-inflatable elastic balloons become squeezed but all balloons 15 of the set C of the self-inflatable elastic balloons will become relaxed, allowed to inflate, and open to flow of air. Therefore, air content of balloons 15 of the set B of the self-inflatable elastic balloons will be forced to flow into the balloons 15 of the set C and into the wearable breathing compartment 27 and into the lungs of the user patient that is using the said wearable breathing compartment 27; balloons 15 of the set A are squeezed, so the gaseous contents of the balloons 15 of the set C cannot exit into the atmosphere. This will comprise the active (i.e., forceful) inhalation step for the user patient that is using the wearable breathing compartment 27.

Referring to FIGS. 3A and 3B, when the compression component 16 is pushed upward, all balloons 15 of the set C of the self-inflatable elastic balloons will become squeezed, thus closed to air flow, but all balloons 15 of both sets A and B of the self-inflatable elastic balloons become relaxed, allowed to inflate, and open to flow of air. With balloons 15 of the set C of the self-inflatable elastic balloons being closed to air flow, inflation of balloons 15 of the set A of the self-inflatable elastic balloons will generate a vacuum within the wearable breathing compartment 27 that is used by a user patient; this will result in suctioning carbon dioxide and other gaseous and non-gaseous content of the alveoli of the lungs of the said user patient and comprises the actively exhalation step for the user patient that is using the wearable breathing compartment 27. The balloons 15 of the set B of the self-inflatable elastic balloons will become filled with atmospheric air to be used for the next inhalation step.

Referring to FIGS. 3A and 3B, as the compression component 16 is pushed downward and upward alternatingly, the Manual Inhalation-Exhalation embodiment of the Active Lung Assist Device will provide active (i.e., forceful) acts of inhalation and exhalation for the user patient that is using the wearable breathing compartment 27.

18. Function of the First Alternative of the Powered Inhalation-Exhalation Embodiment of the Active Lung Assist Device The function and sequences of the steps which results in active (i.e., forceful) acts of inhalation and exhalation for the user patient are the same for both powered and manual inhalation-exhalation embodiments of the Active Lung Assist Device as depicted in FIGS. 3A through 3D; the only difference between the two embodiments is in the use of an electric motor 32 and a cam 33, to cause upward and downward movements of the compression component 16 in the powered embodiment but not in the manual embodiment.

19. Function of the Second Alternative of the Powered Inhalation-Exhalation Embodiment of the Active Lung Assist Device Referring to FIG. 4, with the fluid moving device 34 working, both control valve 50 and valve 52 open, both channels b and c of the directional valve 35 closed, and both channels a and d of the directional valve 35 open, the atmospheric air is taken in through channel a of the directional valve 35, flows through the primary branched tubing network 37, channel d of the directional valve 35, the conditioning unit 55, and enters into the wearable breathing compartment 36 and into the lungs of the user patient that is using the Active Lung Assist Device; this comprises the active (i.e., forceful) inhalation step for the user patient that is using the wearable breathing compartment 36.

Referring to FIG. 4, with the fluid moving device 34 working, both control valve 50 and valve 52 open, both channels b and c of the directional valve 35 open, and both channels a and d of the directional valve 35 closed, carbon dioxide and other gaseous and non-gaseous substances are sucked out of the alveoli and airways of the lungs of the user patient and enter into the wearable breathing compartment 36, flow through the secondary branched tubing network 38, channel b of the directional valve 35, the primary branched tubing network 37, channel c of the directional valve 35, and enter into the atmospheric air through port 44 of the directional valve 35; this comprises the active (i.e., forceful) exhalation step for the user patient that is using the wearable breathing compartment 36.

Referring to FIG. 4, with the actuator of the directional valve 35 making the channels a and d open and channels b and c closed, alternatingly and vice versa, the Second Alternative of the Powered Inhalation-Exhalation Embodiment of the Active Lung Assist Device provides active (i.e., forceful) inhalation and exhalation to the user patient that is using the wearable breathing compartment 36. The time interval during which each pair of the said channels of the directional valve 35 are open or closed can be adjusted to accommodate the respiratory needs of the user patient that uses the wearable breathing compartment 36.

20. Function of the Third Alternative of the Powered Inhalation-Exhalation Embodiment of the Active Lung Assist Device Referring to FIG. 5, atmospheric air is taken from the atmosphere, is pressurized by the fluid moving device 58, and is directed towards the pressurized compartment 56 for storage and further use. Equivalently, oxygen from an oxygen supply source might be used, instead of atmospheric air from the atmosphere, if desired.

Referring to FIG. 5, the pressurized fluctuation minimization tank 73 minimizes pressure fluctuation within the pressurized compartment 56 and other tubing and components of the Active lung Assist Device that are maintained under a positive pressure.

Referring to FIG. 5, the pressure regulation system 65 maintains and monitors a desired adjustable preset positive pressure within the pressurized fluctuation minimization tank 73. Similarly, a pressure regulation system 65 maintains and monitors a desired adjustable preset positive pressure within the pressurized compartment 56 as well.

Referring to FIG. 5, the check valve 72 maintains gas flow only in one direction, i.e., from the pressurizing device 58 towards the pressurized fluctuation minimization tank 73.

Referring to FIG. 5, the filtering component 69 prevents airborne biohazard and particulate substances from entering the fluid moving device 58 or other components of the Active lung Assist Device.

Referring to FIG. 5, the conditioning unit 80 reconditions the pressurized air or oxygen to assure that breathable air or oxygen is available to be supplied to the patient.

Referring to FIG. 5, the valves 79 are used to drain any liquid that might form within the pressurized fluctuation minimization tank 73 or the pressurized compartment 56.

Referring to FIG. 5, multiple sets of the combination of the filtering component 69, the fluid moving device 58 and its driving force, and the check valve 72 are connected, in parallel, to a single pressurized fluctuation minimization tank 73 to assure that pressurized air or oxygen is always available within the pressurized compartment 56 even at times that any of those sets of the filtering component 69, the fluid moving device 58 and its driving force, and the check valve 72 might be shut down for maintenance operation or any other reason.

Referring to FIG. 5, one end of the fluid passing conduit 61 is connected to one point of the pressurized compartment 56, thus allowing pressurized and conditioned air or oxygen to flow through the fluid passing conduit 61. With the Valve 75 open and valve 70 closed, the pressurized and conditioned air or oxygen flows through the fluid passing conduit 61 to enter the port a of the directional valve 60 with further monitoring and maintaining a preset adjustable positive pressure by the pressure regulation system 67.

Referring to FIG. 5, with the directional valve 60 allowing flow from port a to port c and with one end of the branched tubing network 63 being connected to the port c and with another end of the branched tubing network 63 being connected to the wearable breathing compartment 64, and also with the valve 76 and the directional control valve 78 both open, the pressurized and conditioned air or oxygen flows from the port c of the directional valve 60 and enters the wearable breathing compartment 64 to provide assisted inspiration to the patient that is using the wearable breathing compartment 64. The Control valve 77 and its adjacent valve 70 will be open and the function monitoring system 71 will indicate if sufficient breathable air or oxygen is supplied to the wearable breathing compartment 64 or if proper positive pressure is maintained within the wearable breathing compartment 64.

Referring to FIG. 5, if, under any unpredictable circumstances, supply of pressurized and conditioned air or oxygen to the wearable breathing compartment 64 is interrupted, the directional control valve 78 connects the wearable breathing compartment 64 to the atmospheric air, as a safety precaution, so the patient may receive atmospheric air until the cause of interruption is identified and fixed. The port of the directional control valve 78 that connects the wearable breathing compartment 64 to the atmospheric air is not shown in FIG. 5.

Referring to FIG. 5, the fluid moving device 59 generates a vacuum inside the vacuum compartment 57 and other components of the Active lung Assist Device that are to be maintained under a vacuum pressure, by removing and emptying their contents into the outside atmospheric air or into the biohazard collection tanks 82 for proper disposal of the collected biohazard substance at desired time intervals.

Referring to FIG. 5, the isolating valve 83 is used to disconnect its associated biohazard collection tank 82 from the rest of the components of the Active lung Assist Device for maintenance operations or proper disposal of the stored biohazard substances from the biohazard collection tank 82.

Referring to FIG. 5, the vacuum fluctuation minimization tank 74 minimizes fluctuation of the vacuum pressure within the vacuum compartment 57 or other tubing and components of the Active lung Assist Device that are maintained under a vacuum pressure.

Referring to FIG. 5, the pressure regulation system 66 maintains and monitors a desired adjustable preset vacuum pressure within the vacuum fluctuation minimization tank 74. Similarly, a pressure regulation system 66 maintains and monitors a desired adjustable preset vacuum pressure within the vacuum compartment 57 as well.

Referring to FIG. 5, the check valve 81 maintains flow only in one direction, i.e., from the vacuum fluctuation minimization tank 74 towards the fluid moving device 59.

Referring to FIG. 5, one end of the fluid passing conduit 62 is connected to one point of the vacuum compartment 57, thus generating a vacuum in the fluid passing conduit 62 between its point of connection to the vacuum compartment 57 and its point of connection to the port b of the directional valve 60; with its valve 75 being open, its valve 70 being closed, and its pressure regulation system 68 monitoring and maintaining a preset adjustable vacuum pressure within the fluid passing conduit 62. With the directional valve 60 allowing fluid flow from port c to port b and with one end of the branched tubing network 63 being connected to the port c, and with another end of the branched tubing network 63 being connected to the wearable breathing compartment 64, and also with the valve 76 open and the directional control valve 78 open in its normal mode, the vacuum will be extended up to and including the wearable breathing compartment 64 to provide assisted active expiration to the patient that is using the wearable breathing compartment 64. The control valve 77 and its adjacent valve 70 will be open and the function monitoring system 71 will indicate if a proper vacuum is maintained within the branched tubing network 63 and the wearable breathing compartment 64.

Referring to FIG. 5, if, under any unpredictable circumstances, the wearable breathing compartment 64 is not at the right pressure, the directional control valve 78 connects the wearable breathing compartment 64 to the atmospheric air, as a safety precaution, so the patient can breathe on his/her own until the cause of the incorrect pressure is identified and fixed. The port of the directional control valve 78 that connects the wearable breathing compartment 64 to the atmospheric air is not shown in FIG. 5.

Referring to FIG. 5, upon activation of the directional valve 60 by which port c becomes connected to port a and b alternatingly, the wearable breathing compartment 64 becomes under a positive pressure or a vacuum pressure alternatingly, thus provide assisted active inspiration and expiration to the patient that is using the wearable breathing compartment 64.

Referring to FIG. 5, multiple sets of combination of directional valve 60, fluid passing conduit 61, fluid passing conduit 62, branched tubing network 63, wearable breathing compartment 64, pressure regulation system 67, pressure regulation system 68, valves 70, function monitoring system 71, valves 75, valve 76, control valve 77, and the directional control valve 78 can be connected to the pressurized compartment 56 and the vacuum compartment 57 to provide active inhalation and exhalation for multiple user patients (mass user patients) simultaneously. Details of multiple sets connected to the pressurized compartment 56 and the vacuum compartment 57 are not shown in FIG. 5. The Assembly of the components within each of the above sets can be removed from the rest of the components of the Active lung Assist Device, by disconnecting both valves 75 in the fluid passing conduit 61 and the fluid passing conduit 62, to disinfect the said assembly at a central disinfecting facility so the disinfected assembly can be used for a different user patient. Equivalently, disinfecting the said assembly can be done in situ by injecting, circulating, and draining a disinfecting substance through the assembly by closing or opening various valves that are included in the assembly.

21. How to Use the Manual Exhalation Embodiment of the Active Lung Assist Device The Manual Exhalation embodiment of the Active Lung Assist Device, which is depicted in FIG. 1A and FIG. 1B, can provide assisted exhalation and suctioning of a lung at a desired frequency; its suctioning effect can result in emptying alveoli and airways of a lung from any accumulated fluid or prevent excessive accumulation of fluid within the said alveoli and airways when the device is used repeatedly over time. This embodiment can prevent fluid accumulation within alveoli and airways of the lung, thus making it possible for the lung to do gas exchange on its own. This embodiment does not use any powered component; it functions manually.

Referring to FIGS. 1A and 1B, the compression component 4 can be pressed manually on the self-inflatable elastic balloons 2 to deflate them. With the self-inflatable elastic balloons 2 being squeezed and deflated, the open-end point 7 of the tubing network 3 is inserted in the mouth of the user patient. When pressure on the compression component 4 is removed, the self-inflatable elastic balloons 2 expand again and become inflated thus resulting in suctioning gaseous and formed liquid droplets out of the alveoli and airways of the lungs of the user patient. The said steps can be repeated at desired time intervals to keep alveoli and airways of the user patient clear.

22. How to Use the Powered, Non-Automatic, Inhalation-Exhalation Embodiment of the Active Lung Assist Device Referring to FIG. 2, the Powered, Non-Automatic, Inhalation-Exhalation embodiment of the Active Lung Assist Device can provide assisted active inhalation and exhalation to a user patient (thus inflating and suctioning the lungs of the said user patient) at a desired frequency; its suctioning effect can result in emptying alveoli and airways of the said lungs from any accumulated fluid or prevent excessive accumulation of fluid within alveoli and airways of the said lungs when the device is used repeatedly over time, thus making it possible for the said lungs to do gas exchange, on their own, in the absence of any accumulated fluid within the lungs.

Referring to FIG. 2, with the fluid moving device 8 working and valve 13 open, the first wearable breathing compartment 11 can be placed on the mouth and nose of the user patient to provide active exhalation and suction gases and liquid droplets from lungs of the user patient. The valve 13 is open to a degree to generate a safe pressure and flow rate within the first wearable breathing compartment 11 and to prevent any negative impact on the alveoli and airways of the lungs of the user patient.

Referring to FIG. 2, with the fluid moving device 8 working and valve 13 open, the second wearable breathing compartment 12 can be placed on the mouth and nose of the user patient to provide active inhalation to the said user patient. The valve 13 is open to a degree to generate a safe pressure and flow rate within the second wearable breathing compartment 12 and to prevent any negative impact on the alveoli and airways of the lungs of the user patient.

Referring to FIG. 2, with the fluid moving device 8 working and valve 13 open, the first wearable breathing compartment 11 and the second wearable breathing compartment 12 can be placed on the mouth and nose of the user patient, alternatingly, to provide active exhalation and inhalation, alternatingly, to the user patient over a desired time period.

23. How to Use the Manual Inhalation-Exhalation Embodiment of the Active Lung Assist Device Referring to FIGS. 3A, 3B, and 3C, when the compression component 16 is pushed downward, all balloons 15 of both sets A and B of the self-inflatable elastic balloons become squeezed but all balloons 15 of the set C of the self-inflatable elastic balloons will become relaxed, allowed to inflate, and open to flow of air. Therefore, air content of balloons 15 of the set B of the self-inflatable elastic balloons will be forced to flow into the wearable breathing compartment 27 and into the lungs of the user patient that is using the said wearable breathing compartment 27; this will comprise the active (i.e., forceful) inhalation step for the user patient that is using the wearable breathing compartment 27.

Referring to FIGS. 3A, 3B, and 3C, when the compression component 16 is pushed upward, all balloons 15 of the set C of the self-inflatable elastic balloons will become squeezed, thus closed to air flow, but all balloons 15 of both sets A and B of the self-inflatable elastic balloons become relaxed, allowed to inflate, and open to flow of air. With balloons 15 of the set C of the self-inflatable elastic balloons being closed to air flow, inflation of balloons 15 of the set A of the self-inflatable elastic balloons will generate a vacuum within the wearable breathing compartment 27 that is used by a user patient; this will result in suctioning carbon dioxide and other gaseous and non-gaseous content of the alveoli of the lungs of the said user patient and comprises the actively exhalation step for the user patient that is using the wearable breathing compartment 27. The balloons 15 of the set B of the self-inflatable elastic balloons will become filled with atmospheric air to be used for the next inhalation step.

Referring to FIGS. 3A, 3B, and 3C, with the wearable breathing compartment 27 placed on the mouth and nose of the user patient, and the compression component 16 is pushed downward and upward, alternatingly over a time period, the Manual Inhalation-Exhalation embodiment of the Active Lung Assist Device can provide active inhalation and exhalation, alternatingly over the said time period, to the user patient.

24. How to Use the First Alternative of the Powered Inhalation-Exhalation Embodiment of the Active Lung Assist Device Referring to FIG. 3D, the First Alternative of the Powered Inhalation-Exhalation Embodiment of the Active Lung Assist Device, is different from the Manual Inhalation-Exhalation embodiment of the Active Lung Assist Device in which the alternating upward and downward movements of the compression component 16 is caused by a powered device such as an electric motor, or any other device which might use any other source of power, and a motion conversion mechanism which converts the power of the electric motor, or any other device which uses any other source of power, to the alternating upward and downward movements of the compression component 16. The detailed sketches that are shown in FIGS. 3B and 3C also apply to the First Alternative of the Powered Inhalation-Exhalation Embodiment of the Active Lung Assist Device that is shown in FIG. 3D.

Referring to FIGS. 3B, 3C, and 3D, with the wearable breathing compartment 27 placed on the mouth and nose of the user patient and by the functioning of the electric motor 32 and the cam 33 causing the compression component 16 to move upward and downward, alternatingly over a time period, the First Alternative of the Powered Inhalation-Exhalation Embodiment of the Active Lung Assist Device can provide active inhalation and exhalation, alternatingly over the said time period, to the user patient.

Referring to FIGS. 3B and 3C, the wearable breathing compartment 27 may alternatively be placed in the airways of the user patient, if desired, to provide safe and active expiration and inspiration to the said user patient.

25. How to Use the Second Alternative of the Powered Inhalation-Exhalation Embodiment of the Active Lung Assist Device Referring to FIG. 4, with the fluid moving device 34 working, both control valve 50 and valve 52 open, both channels b and c of the directional valve 35 closed, and both channels a and d of the directional valve 35 open, the atmospheric air is taken in through channel a of the directional valve 35, flows through the primary branched tubing network 37, channel d of the directional valve 35, the conditioning unit 55, and enters into the wearable breathing compartment 36 and into the lungs of the user patient; this comprises the active (i.e., forceful) inhalation step for the user patient that is using the wearable breathing compartment 36.

Referring to FIG. 4, with the fluid moving device 34 working, both control valve 50 and valve 52 open, both channels b and c of the directional valve 35 open, and both channels a and d of the directional valve 35 closed, carbon dioxide and other gaseous and non-gaseous substances are sucked out of the alveoli and airways of the lungs of the user patient and enter into the wearable breathing compartment 36, flow through the secondary branched tubing network 38, channel b of the directional valve 35, the primary branched tubing network 37, channel c of the directional valve 35, and enter into the atmospheric air through port 44 of the directional valve 35; this comprises the active (i.e., forceful) exhalation step for the user patient that is using the wearable breathing compartment 36.

Referring to FIG. 4, with the actuator of the directional valve 35 making the channels a and d open and channels b and c closed, alternatingly and vice versa, the Second Alternative of the Powered Inhalation-Exhalation Embodiment of the Active Lung Assist Device provides active (i.e., forceful) inhalation and exhalation to the user patient that is using the wearable breathing compartment 36. The time interval during which each pair of the said channels of the directional valve 35 are open or closed can be adjusted to accommodate the respiratory needs of the user patient that uses the wearable breathing compartment 36.

Referring to FIG. 4, the drain valves 53 and the vent valves 54 can be used to drain or vent the Second Alternative of the Powered Inhalation-Exhalation Embodiment of the Active Lung Assist Device as needed.

Referring to FIG. 4, the wearable breathing compartment 36 may alternatively be placed in the airways of the user patient, if desired, to provide safe and active expiration and inspiration to the said user patient.

26. How to Use the Third Alternative of the Powered Inhalation-Exhalation Embodiment of the Active Lung Assist Device Referring to FIG. 5, the Third Alternative of the Powered Inhalation-Exhalation Embodiment of the Active Lung Assist Device is equipped with a pressurized compartment 56, that contains breathable gas at a desired pressure, and a vacuum compartment 57 that is maintained at a desired vacuum pressure.

Referring to FIG. 5, the breathable air that is contained within the pressurized compartment 56 can flow towards the port a of the directional valve 60, the fluid that becomes available at port b of the directional valve 60 can flow towards the vacuum compartment 57, and the breathable gas or any other fluid that might become available at port c of the directional valve 60 can flow towards the wearable breathing compartment 64 and vice versa.

Referring to FIG. 5, with the wearable breathing compartment 64 being placed on the mouth and nose of the user patient and with the directional valve 60 connecting its port c to either port a or port b, alternatingly, the wearable breathing compartment 64 communicates with the pressurized compartment 56 and the vacuum compartment 57, alternatingly, and thus provides active inspiration and expiration to the user patient, alternatingly.

Referring to FIG. 5, the wearable breathing compartment 64 may alternatively be placed in the airways of the user patient, if desired, to provide safe and active expiration and inspiration to the said user patient.

Referring to FIG. 5, multiple sets of the wearable breathing compartment 64 and the directional valve 60, with their other associated components as seen in FIG. 5, can be connected to the pressurized compartment 56 and the vacuum compartment 57 to provide active expiration and inspiration to multiple user patients simultaneously.

Referring to FIG. 5, the valves and instrumentation associated with each branching set of the wearable breathing compartment 64 and the directional valve 60 can be used to adjust inspiratory and expiratory fluid pressure and flow rates in each branch to accommodate respiratory needs of various user patients.

Thus it will be appreciated by those skilled in the art that the present invention is not restricted to the particular preferred embodiments described with reference to the drawings, and that variations may be made therein without departing from the scope of the present invention as defined in the appended claims and equivalents thereof

The invention claimed is:

1. An apparatus, comprising:
   first, second and third sets of balloons in a base compartment;
   a compression component on or over the balloons, configured to expel air from the balloons when pressed against the balloons, wherein the first and second sets of balloons are between the compression component and the base compartment;
   a tubing network connected to the first, second and third sets of balloons, configured to carry the air from the first and/or second sets of balloons and to the third set of balloons;
   a wearable breathing compartment at an outlet of the tubing network;
   a first check valve in the tubing network between the third set of balloons and the wearable breathing compartment;
   a second check valve in the tubing network between the wearable breathing compartment and the first and/or second sets of balloons;
   one or more third check valves between the first set of balloons and atmospheric air;
   one or more fourth check valves between the second set of balloons and the atmospheric air;
   a cover over the compression component, configured to secure the compression component to the base compartment, wherein the third set of balloons is between the compression component and the cover; and
   one or more motion restricting components in the base compartment, configured to control an extent of movement of the compression component and prevent damage to other components inside the base compartment.

2. The apparatus according to claim 1, comprising a plurality of the motion restricting components.

3. The apparatus according to claim 1, wherein the base compartment comprises one or more walls with a plurality of openings therein, and the tubing network comprises a plurality of tube segments, each of which (i) pass through a corresponding one of the openings in the walls of the base compartment and (ii) have an end connected to a corresponding one of the balloons.

4. The apparatus according to claim 1, wherein the compression component has at least two dimensions smaller than corresponding dimensions of the base compartment.

5. The apparatus according to claim 1, further comprising:
   a plurality of bolts passing through the base compartment and the compression component, the compression component being configured to move up and down along the plurality of bolts; and
   a plurality of springs in a 1:1 relationship with the plurality of bolts, wherein the plurality of springs are compressed as the compression component moves toward the base compartment.

6. The apparatus according to claim 5, wherein the base compartment comprises first and second opposing walls, each with a slot therein, and the compression component passes through each of the slots.

7. The apparatus according to claim 5, wherein each of the third set of balloons has one side or end attached and/or secured to the cover and an opposite side or end attached and/or secured to the compression component, and the tubing network connects an end of each of the first set of balloons to an end of each of the second set of balloons.

* * * * *